(12) United States Patent
Matsunaga et al.

(10) Patent No.: US 7,662,193 B2
(45) Date of Patent: Feb. 16, 2010

(54) HAIR DYE COMPOSITION

(75) Inventors: Kenichi Matsunaga, Sumida-ku (JP); Hiromi Saimiya, Sumida-ku (JP); Dominic Pratt, Darmstadt (DE); Yasuhiro Ishiwata, Minamiashigara (JP)

(73) Assignees: Kao Corporation, Tokyo (JP); Fujifilm Corporation, Tokyo (JP)

( * ) Notice: Subject to any disclaimer, the term of this patent is extended or adjusted under 35 U.S.C. 154(b) by 73 days.

(21) Appl. No.: 11/815,383

(22) PCT Filed: Feb. 3, 2006

(86) PCT No.: PCT/JP2006/301877

§ 371 (c)(1), (2), (4) Date: Aug. 2, 2007

(87) PCT Pub. No.: WO2006/082929

PCT Pub. Date: Aug. 10, 2006

(65) Prior Publication Data

US 2009/0049622 A1 Feb. 26, 2009

(30) Foreign Application Priority Data

Feb. 4, 2005 (JP) .............................. 2005-029183

(51) Int. Cl.
*A61Q 5/10* (2006.01)
(52) U.S. Cl. ........................ 8/405; 8/570; 8/571; 8/573; 8/576
(58) Field of Classification Search .................. 8/405, 8/570, 571, 573, 576
See application file for complete search history.

(56) References Cited

U.S. PATENT DOCUMENTS

2004/0019982 A1* 2/2004 Pratt et al. ..................... 8/405

FOREIGN PATENT DOCUMENTS

| JP | 11 512440 | 10/1999 |
| JP | 2003 0342139 | 12/2003 |

OTHER PUBLICATIONS

STIC Search Report dated Feb. 24, 2009.*

\* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

Provided is a hair dye composition containing a dissociative direct dye (1):

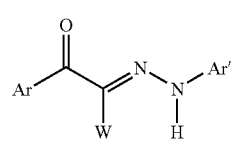

(1)

(wherein Ar represents an aromatic group or heterocyclic aromatic group which may have a substituent, Ar' represents an aromatic group which may be substituted by an alkyl group or an electron drawing group, or a specific heterocyclic aromatic group, and W represents an electron drawing group); or salt thereof.

8 Claims, No Drawings

HAIR DYE COMPOSITION

FIELD OF THE INVENTION

The present invention relates to a hair dye composition containing a dissociative direct dye.

BACKGROUND OF THE INVENTION

Hair dyes can be classified by the dye to be used or according to whether they have bleaching action on melanin or not. Typical examples include a two-part permanent hair dye composed of a first part containing an alkali agent, an oxidation dye and optionally, a direct dye such as nitro dye and a second part containing an oxidizing agent; and one-part semi-permanent hair dye containing an organic acid or an alkali agent, and at least one direct dye such as acid dye, basic dye or nitro dye.

The two part permanent hair dye however has a drawback that color tone imparted by an oxidation dye is not so vivid. Another drawback is that the color of the hair dyed with a vivid-color producing nitro dye ordinarily employed as a direct dye markedly fades over time and becomes dull soon even if the color tone just after dyeing is very vivid (for example, refer to Patent Document 1). In order to produce a vivid color, permanent hair dyes therefore contain various direct dyes such as cationic direct dyes and nitro dyes in combination.

Direct dyes available at present however do not bring about sufficient effects. The kind of direct dyes to be used in combination with an oxidation dye is limited because they are required to have stability against alkaline peroxides during the hair dyeing process. In any case, fading progresses very rapidly owing to the loss of a direct dye caused by washing or exposure to light and this phenomenon is notable in damaged hair or porous hair (hair having pores therein).

The present inventors therefore proposed an azo dye having a dissociative proton as a useful direct dye capable of overcoming the above-described problem (for example, refer to Patent Documents 2 and 3). This direct dye however needs to be improved to have excellent resistance to light, washing, sweat, friction and heat, and needs to be stable against an alkalizing agent and oxidizing agent.

[Patent Document 1] JP-A-6-271435
[Patent Document 2] JP-A-2003-342139
[Patent Document 3] JP-A-2004-107343

DISCLOSURE OF THE INVENTION

The present invention provides a hair dye composition containing a dissociative direct dye represented by the following formula (1):

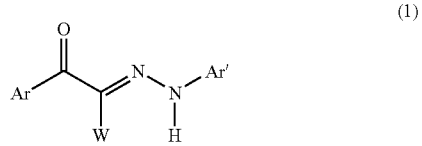

(1)

(wherein, Ar and Ar' each has none of a carboxy group, sulfo group and quaternary ammonium group;

Ar represents an aromatic group or heterocyclic aromatic group which may have a substituent, Ar' represents an aromatic group which may have, as a substituent, an alkyl group or electron withdrawing group, or a heterocyclic aromatic group represented by any one of the following formulas (Cp-1) to (Cp-4):

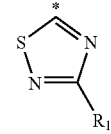

(Cp-1)

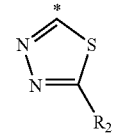

(Cp-2)

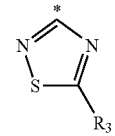

(Cp-3)

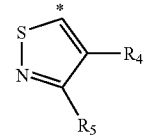

(Cp-4)

(* means a bonding position to the nitrogen atom in the formula (1), $R_1$ to $R_5$ each represents a hydrogen atom, $C_1$-$C_8$ alkyl group, alkoxy group, alkoxyalkyl group, hydroxyalkyl group, aryl group, aryloxy group, alkylthio group or arylthio group, and $R_4$ and $R_5$ may be the same or different and may be coupled to form a saturated ring, aromatic ring or heteroaromatic ring which may have a substituent together with two vicinal carbon atoms);

and W represents an electron withdrawing group); or salt thereof.

The present invention also provides a hair dyeing method, which includes applying the above-described hair dye composition to the hair.

MODE FOR CARRYING OUT THE INVENTION

The present invention relates to a hair dye composition capable of firmly imparting a vivid color to the hair without causing decomposition of the dye, having excellent resistance to light, washing, sweat, friction and heat, being stable to an alkalizing agent and oxidizing agent, having a high dyeing power, and having less fading over time; and a hair dyeing method using the hair dye composition.

The present inventors have found that a hair dye composition containing a dissociative direct dye represented by the formula (1) can firmly impart a vivid color selected from a wide range of colors to the hair without causing decomposition of the dye during hair dyeing and it has excellent resistance to light, washing, sweat, friction and heat.

The dissociative direct dye represented by the formula (1) for use in the present invention typically imparts a desired hue to the hair by converting an oxo group at the α-position of the aromatic ring or heteroaromatic ring into a hydroxy group in the hair dye system based on the keto-enol tautomerism and dissociating a proton under use conditions to change the hue. A tautomer includes not only a keto-enol type but, for example, a tautomer via Ar'. Moreover, it includes not only a tautomer in the non-dissociated form as shown in the below-described formula, but that in the dissociated form.

pound, such as 1-pyrazolyl, 1-imidazolyl, 2-furyl, 2-thienyl, 4-pyrimidinyl and 2-benzothiazolyl), cyano group, hydroxy group, nitro group, alkoxy groups (linear, branched or cyclic, $C_{1-10}$, preferably $C_{1-6}$ alkoxy groups such as methoxy, ethoxy, isopropoxy, t-butoxy, cyclopentyloxy, 2-buten-1-yloxy and 2-methoxyethoxy), aryloxy groups ($C_{6-12}$, prefer-

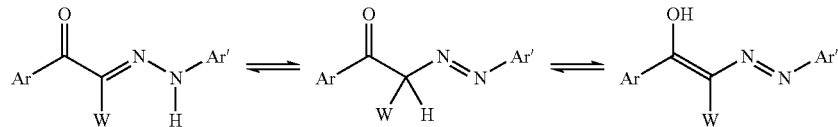

In the formula (1), Ar and Ar' each does not have any of carboxy group, sulfo group or quaternary ammonium group. The terms "carboxy group" and "sulfo group" as used herein each includes not only acid type groups but also neutral type groups such as —COONa and —SO₃Na. This therefore means that the direct dye (1) does not have any of carboxy group, sulfo group or quaternary ammonium group regardless whether it is an acid type or neutral type.

In the formula (1), examples of the aromatic group represented by Ar include phenyl and naphthyl groups, while those of the heterocyclic aromatic group represented by Ar include pyridyl, pyridazinyl, pyrimidinyl, pyrazinyl, pyrrolyl, furyl, thiophenyl, oxazolyl, isoxazolyl, thiazolyl, isothiazolyl, imidazolyl, pyrazolyl, quinolyl, isoquinolyl, quinazolyl and indolyl groups.

The above-described aromatic or heterocyclic aromatic group may have at least one substituent. When it has two or more substituents, they may be the same or different. Examples of groups by which Ar may be substituted include halogen atoms, alkyl groups (including cycloalkyl groups), alkenyl groups (including cycloalkenyl groups), alkynyl groups, aryl groups, heterocyclic groups, cyano group, hydroxy group, nitro group, alkoxy groups, aryloxy groups, silyloxy group, heterocyclic oxy groups, acyloxy groups, carbamoyloxy groups, alkoxycarbonyloxy groups, aryloxycarbonyloxy groups, amino groups (including anilino group), acylamino groups, aminocarbonylamino groups, alkoxycarbonylamino groups, aryloxycarbonylamino groups, sulfamoylamino groups, alkylsulfonylamino groups, arylsulfonylamino groups, mercapto group, alkylthio groups, arylthio groups, heterocyclic thio groups, sulfamoyl groups, alkylsulfinyl groups, arylsulfinyl groups, alkylsulfonyl groups, arylsulfonyl groups, acyl groups, alkoxycarbonyl groups, aryloxycarbonyl groups, carbamoyl group, arylazo groups, heterocyclic azo groups, imido groups, phosphino groups, phosphinyl groups, phosphinyloxy groups, phosphinylamino groups and silyl groups.

Specific examples thereof include halogen atoms (such as chlorine, bromine and iodine atoms), alkyl groups (linear, branched or cyclic $C_{1-10}$, preferably $C_{1-6}$ alkyl groups such as methyl, ethyl, n-propyl, isopropyl, t-butyl, n-octyl, 2-chloroethyl, 2-cyanoethyl, 2-ethylhexyl, cyclopropyl and cyclopentyl), alkenyl groups (linear, branched or cyclic $C_{2-10}$, preferably $C_{2-6}$ alkenyl groups such as vinyl, allyl, prenyl and cyclopenten-1-yl), alkynyl groups ($C_{2-10}$, preferably $C_{2-6}$ alkynyl groups such as ethynyl and propargyl), aryl groups ($C_{6-12}$, preferably $C_{6-8}$ aryl groups such as phenyl, p-tolyl, naphthyl, 3-chlorophenyl and 2-aminophenyl), heterocyclic groups (monovalent $C_{1-12}$, preferably $C_{2-6}$ groups available by removing one hydrogen atom from 5-membered or 6-membered aromatic or nonaromatic heterocyclic comably $C_{6-8}$ aryloxy groups such as phenoxy, 2-methylphenoxy, 4-t-butylphenoxy and 3-nitrophenoxy), silyloxy groups ($C_{3-10}$, preferably $C_{3-6}$ silyloxy groups such as trimethylsilyloxy and t-butyldimethylsilyloxy), heterocyclic oxy groups ($C_{1-12}$, preferably $C_{2-6}$ heterocyclic oxy groups such as 1-phenyltetrazol-5-oxy and 2-tetrahydropyranyloxy), acyloxy groups ($C_{1-12}$, preferably $C_{1-8}$ acyloxy groups such as formyloxy, acetyloxy, pivaloyloxy, benzoyloxy and p-methoxyphenylcarbonyloxy), carbamoyloxy groups ($C_{1-10}$, preferably $C_{1-6}$ carbamoyloxy groups such as N,N-dimethylcarbamoyloxy, N,N-diethylcarbamoyloxy, morpholinocarbonyloxy, and N,N-octylcarbamoyloxy), alkoxycarbonyloxy groups ($C_{2-10}$, preferably $C_{2-6}$ alkoxycarbonyloxy groups such as methoxycarbonyloxy, ethoxycarbonyloxy, t-butoxycarbonyloxy and n-octyloxycarbonyloxy), aryloxycarbonyloxy groups ($C_{7-12}$, preferably $C_{7-10}$ aryloxycarbonyloxy groups such as phenoxycarbonyloxy and p-methoxyphenoxycarbonyloxy), amino groups (amino groups and $C_{1-10}$, preferably $C_{1-6}$ alkylamino groups, $C_{6-12}$, preferably $C_{6-8}$ anilino groups, and $C_{1-12}$, preferably $C_{2-6}$ heterocyclic amino groups, such as amino, methylamino, dimethylamino, anilino, N-methylanilino, diphenylamino, imidazol-2-ylamino and pyrazol-3-ylamino), acylamino groups ($C_{1-10}$, preferably $C_{1-6}$ alkylcarbonylamino groups, $C_{6-12}$, preferably $C_{6-8}$ arylcarbonylamino groups, and $C_{2-12}$, preferably $C_{2-6}$ heterocyclic carbonylamino groups, such as formylamino, acetylamino, pivaloylamino, benzoylamino, pyridine-4-carbonylamino, and thiophene-2-carbonylamino), aminocarbonylamino groups ($C_{1-12}$, preferably $C_{1-6}$ aminocarbonylamino groups such as carbamoylamino, N,N-dimethylaminocarbonylamino, N,N-diethylaminocarbonylamino, and morpholin-4-ylcarbonylamino), alkoxycarbonylamino groups ($C_{2-10}$, preferably $C_{2-6}$ alkoxycarbonylamino groups such as methoxycarbonylamino, ethoxycarbonylamino and t-butoxycarbonylamino), aryloxycarbonylamino groups ($C_{7-12}$, preferably $C_{7-9}$ aryloxycarbonylamino groups such as phenoxycarbonylamino, p-chlorophenoxycarbonylamino and 4-methoxyphenoxycarbonylamino), sulfamoylamino groups ($C_{0-10}$, preferably $C_{0-6}$ sulfamoylamino groups such as sulfamoylamino, N,N-dimethylaminosulfonylamino and N-(2-hydroxyethyl)sulfamoylamino), alkylsulfonylamino groups ($C_{1-10}$, preferably $C_{1-6}$ alkylsulfonylamino groups such as methylsulfonylamino and butylsulfonylamino), arylsulfonylamino groups ($C_{6-12}$, preferably $C_{6-8}$ arylsulfonylamino groups such as phenylsulfonylamino, 2,3,5-trichlorophenylsulfonylamino and p-methylphenylsulfonylamino), mercapto group, alkylthio groups ($C_{1-10}$, preferably $C_{1-6}$ alkylthio groups such as methylthio, ethylthio and butylthio), arylthio groups ($C_{6-12}$, preferably $C_{6-8}$ arylthio groups such as phenylthio, p-chlorophenylthio and m-methoxythio), heterocyclic thio groups ($C_{2-10}$, preferably $C_{1-6}$ heterocyclic thio groups such as 2-benzothiazolylthio and 1-phenyltetrazol-5-ylthio), sulfamoyl groups ($C_{0-10}$, preferably $C_{0-6}$ sulfamoyl groups such as sulfamoyl, N-ethylsulfamoyl, N,N-dimethylsulfamoyl, N-acetylsulfamoyl and N-benzoylsulfamoyl), alkylsulfinyl groups ($C_{1-10}$, preferably $C_{1-6}$ alkylsulfinyl groups such as methylsulfinyl and ethylsulfinyl), arylsulfinyl groups ($C_{6-12}$, preferably $C_{6-8}$ arylsulfinyl groups such as phenylsulfinyl and p-methylphenylsulfinyl), alkylsulfonyl groups ($C_{1-10}$, preferably $C_{1-6}$ alkylsulfonyl groups such as methylsulfonyl and ethylsulfonyl), arylsulfonyl groups ($C_{6-12}$, preferably $C_{6-8}$ arylsulfonyl groups such as phenylsulfonyl and p-chlorophenylsulfonyl), acyl groups (formyl group, $C_{2-10}$, preferably $C_{2-6}$ alkylcarbonyl groups and $C_{7-12}$, preferably $C_{7-9}$ arylcarbonyl groups such as acetyl, pivaloyl, 2-chloroacetyl, benzoyl and 2,4-dichlorobenzoyl), alkoxycarbonyl groups ($C_{2-10}$, preferably $C_{2-6}$ alkoxycarbonyl groups such as methoxycarbonyl, ethoxycarbonyl, t-butoxycarbonyl and isobutyloxycarbonyl), aryloxycarbonyl groups ($C_{7-12}$, preferably $C_{7-9}$ aryloxycarbonyl groups such as phenoxycarbonyl, 2-chlorophenoxycarbonyl, 3-nitrophenoxycarbonyl and 4-t-butylphenoxycarbonyl), carbamoyl groups ($C_{1-10}$, preferably $C_{1-6}$ carbamoyl groups such as carbamoyl, N-methylcarbamoyl, N,N-dimethylcarbamoyl, N-(2-hydroxyethyl)carbamoyl and N-(methylsulfonyl)carbamoyl), arylazo groups ($C_{6-12}$, preferably $C_{6-8}$ arylazo groups such as phenylazo and p-chlorophenylazo), heterocyclic azo groups ($C_{1-10}$, preferably $C_{1-6}$ heterocyclic azo groups such as pyrazol-3-ylazo, thiazol-2-ylazo and 5-ethylthio-1,3,4-thiadiazol-2-ylazo), imido groups ($C_{2-10}$, preferably $C_{4-8}$ imido groups such as N-succinimide and N-phthalimide), phosphino groups ($C_{2-12}$, preferably $C_{2-6}$ phosphino groups such as dimethylphosphino, diphenylphosphino and methylphenoxyphosphino), phosphinyl groups ($C_{2-12}$, preferably $C_{2-6}$ phosphinyl groups such as phosphinyl and diethoxyphosphinyl), phosphinyloxy groups ($C_{2-12}$, preferably $C_{2-6}$ phosphinyloxy groups such as diphenoxyphosphinyloxy and dibutoxyphosphinyloxy), phosphinylamino groups ($C_{2-12}$, preferably $C_{2-6}$ phosphinylamino groups such as dimethoxyphosphinylamino and dimethylaminophosphinylamino), and silyl groups ($C_{3-12}$, preferably $C_{3-8}$ silyl groups such as trimethylsilyl, t-butyldimethylsilyl and phenyldimethylsilyl).

When these groups can be substituted, they may have a substituent further. Groups by which they may be substituted are similar to the above-described groups by which Ar may be substituted. When they have two or more substituents, the substituents may be the same or different.

Of the substituents in Ar, preferred examples include halogen atoms, alkyl groups, aryl groups, heterocyclic groups, cyano group, hydroxy group, nitro group, alkoxy groups, aryloxy groups, amino groups (including anilino groups), acylamino groups, aminocarbonylamino groups, alkoxycarbonylamino groups, alkylsulfonylamino groups, arylsulfonylamino groups, alkylthio groups, arylthio groups, heterocyclic thio groups, sulfamoyl groups, alkylsulfonyl groups, arylsulfonyl groups, acyl groups, alkoxycarbonyl groups and carbamoyl groups, with halogen atoms, alkyl groups, cyano group, hydroxy group, nitro group, alkoxy groups, amino groups (including anilino groups), acylamino groups, alkylsulfonylamino groups and carbamoyl groups being more preferred.

As Ar, a phenyl group which may be substituted by a halogen atom, alkyl group, alkoxy group, cyano group, acylamino group or carbamoyl group is preferred.

Ar' represents an aromatic group which may have an alkyl group or electron withdrawing group as a substituent, or heterocyclic aromatic group represented by any one of the below-described formulas (Cp-1) to (Cp-4):

(Cp-1)

(Cp-2)

(Cp-3)

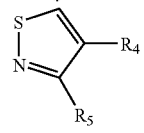

(Cp-4)

The aromatic group represented by Ar' is, for example, a phenyl group or a naphthyl group. Examples of the alkyl group by which the aromatic group may be substituted include $C_{1-10}$, preferably $C_{1-6}$ alkyl groups such as methyl, ethyl, n-propyl, isopropyl, t-butyl, n-octyl, 2-chloroethyl, 2-cyanoethyl, 2-ethylhexyl, cyclopropyl, and cyclopentyl groups. Examples of the electron withdrawing group by which the aromatic ring may be substituted include chlorine atom, bromine atom, iodine atom, cyano group, alkoxycarbonyl groups, carbamoyl groups, alkylaminocarbonyl groups, dialkylaminocarbonyl groups, sulfamoyl groups, alkylaminosulfonyl groups, dialkylaminosulfonyl groups and acyl groups. Of these, cyano group, alkoxycarbonyl groups and carbamoyl groups are even more preferred. When Ar' is a phenyl group substituted by two or more alkyl groups or electron withdrawing groups as substituents, these substituents may be the same or different.

In the formulas (Cp-1) to (Cp-4), $R_1$ to $R_5$ each represents a hydrogen atom, $C_{1-8}$ alkyl group, alkoxy group, alkoxyalkyl group, hydroxyalkyl group, aryl group, aryloxy group, alkylthio group or arylthio group. $R_4$ and $R_5$ may be the same or different. Specific preferred examples thereof are the groups having 1 to 6 carbon atoms among those described for Ar of the formula (1).

In the heterocyclic aromatic group represented by (Cp-4), $R_4$ and $R_5$ may each represent the above-described group or may be coupled to form a saturated ring, aromatic ring or heteroaromatic ring together with two vicinal carbon atoms. These rings may have substituents similar to those described for Ar of the formula (1). Examples include 2,1-benzisothiazol-3-yl, isothiazolo[4,3-b]pyridin-3-yl, isothiazolo[4,3-c]pyridin-3-yl, isothiazolo[3,4-c]pyridin-3-yl, isothiazolo[3,4-b ]pyridin-3-yl, isothiazolo[4,3-c]pyridazin-3-yl, isothiazolo[4,3-d]pyrimidin-3-yl, isothiazolo[3,4-b]pyrazin-3-yl, isothiazolo[3,4-d]pyridazin-3-yl, isothiazolo[3,4-d]pyrimidin-3-yl, and isothiazolo[3,4-c]pyridazin-3-yl groups (structural formulas of which will be shown below).

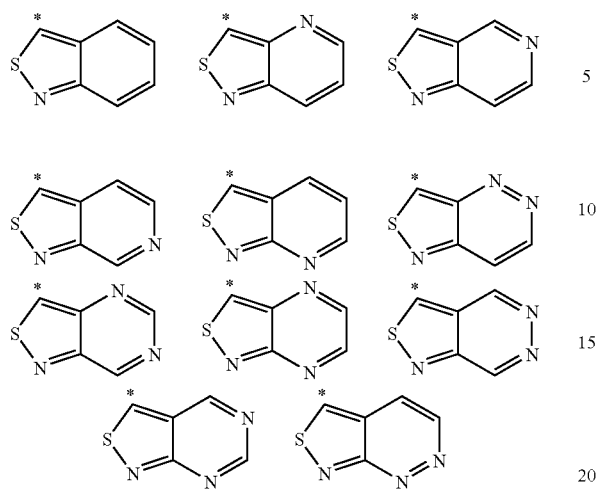

[* means a bonding position to the nitrogen atom in the formula (1).]

As Ar', preferred are phenyl groups which may be substituted by a halogen atom, alkyl group, alkoxy group, cyano group, acylamino group, aminocarbonylamino group, alkoxycarbonylamino group, aryloxycarbonylamino group, sulfamoylamino group, alkylsulfonylamino group, arylsulfonylamino group, alkoxycarbonyl group, sulfamoyl group or carbamoyl group, or heterocyclic aromatic groups represented by any one of the formulas (Cp-1), (Cp-2) and (Cp-4).

In the formula (1), examples of the electron withdrawing group represented by W include electron withdrawing groups having a Hammett $\sigma_p$ value of 0.1 or greater such as a fluorine atom, chlorine atom, bromine atom, iodine atom, cyano group, nitro group; alkoxycarbonyl groups, carbamoyl groups, alkylaminocarbonyl groups, dialkylaminocarbonyl groups, sulfamoyl groups, alkylaminosulfonyl groups, dialkylaminosulfonyl groups, acyl groups, acylamino groups, aminocarbonylamino groups, sulfamoylamino groups, alkylsulfonylamino groups and arylsulfonylamino groups, which may each be substituted by one or more hydroxy groups. Of these, nitro group, cyano group, acylamino groups, aminocarbonylamino groups, sulfamoylamino groups, alkylsulfonylamino groups, arylsulfonylamino groups, sulfamoyl groups, and carbamoyl groups are preferred, with acyl groups and cyano groups being more preferred from the viewpoint of the dyeing strength. The Hammett's empirical rule was advocated by L. P. Hammett in 1935 in order to quantitatively discuss the influence of a substituent on the reaction or equilibrium of a benzene derivative and its validity is now recognized widely. The substituent constants determined by the Hammett's rule are $\sigma_p$ and $\sigma_m$ values. These values are found generally in many books and described in detail, for example, in *Lange's Handbook of Chemistry,* 12 ed., 1979, ed. J. A. Dean (published by McGraw-Hill), *Journal of Japanese Chemistry*, Extra Number, 122, 96-103 (1979) (published by Nankodo), and *Chemical Review*, 91, 165-195 (1991).

Specific examples of the direct dyes of the present invention represented by the formula (1) include those having a structure as shown below.

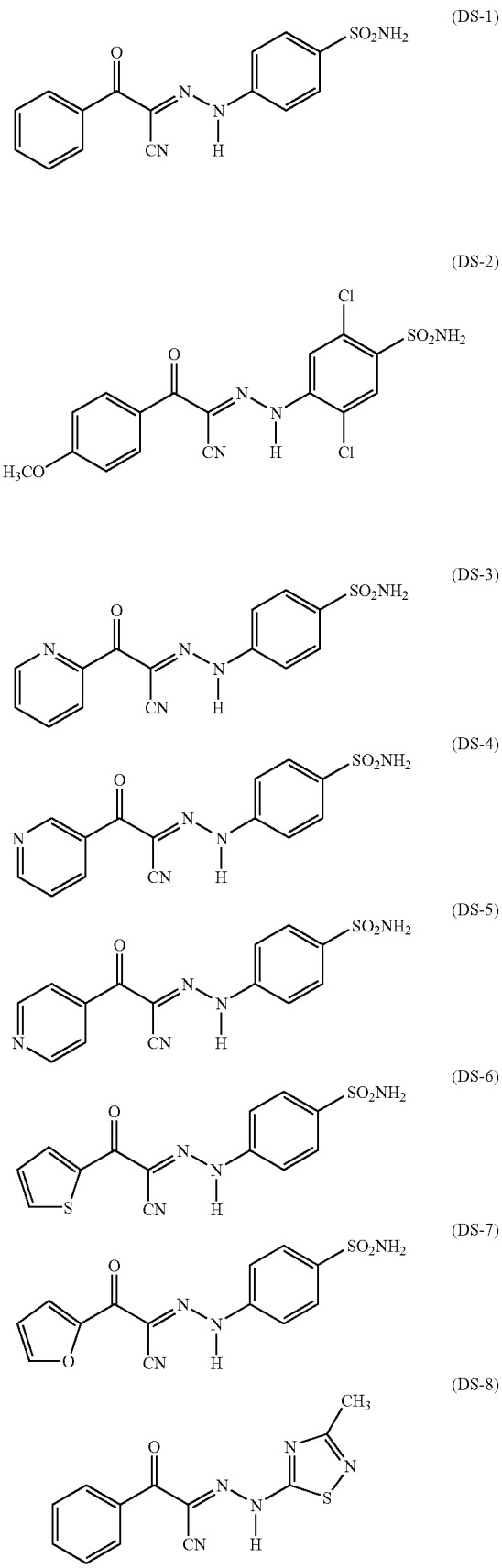

-continued
(DS-9)
(DS-10)
(DS-11)
(DS-12)
(DS-13)
(DS-14)
(DS-15)
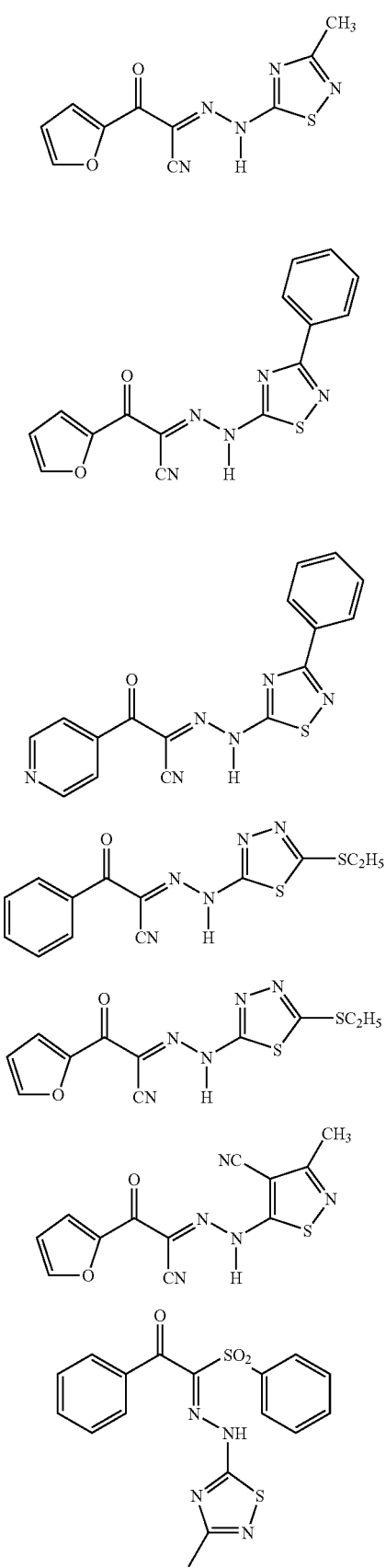
-continued
(DS-16)
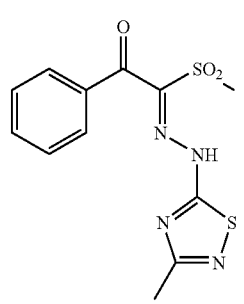
(DS-17)
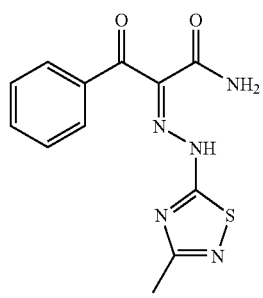
(DS-18)
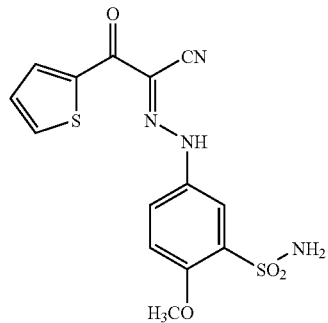
(DS-19)
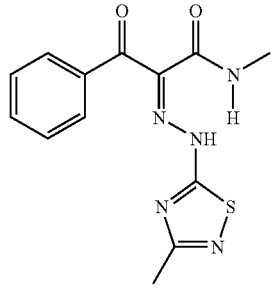
(DS-20)
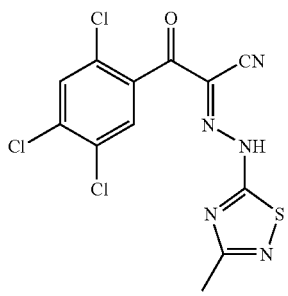

-continued
(DS-21)
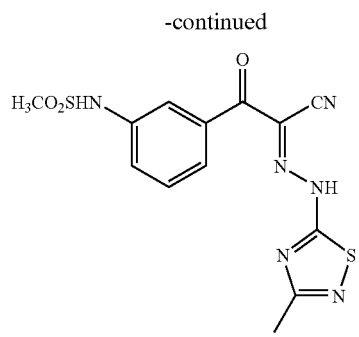
(DS-22)
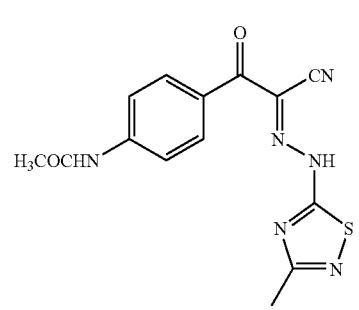
(DS-23)
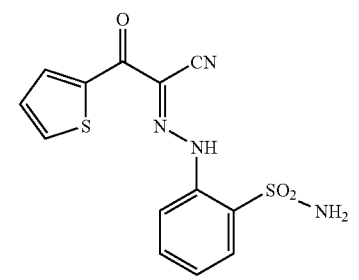
(DS-24)
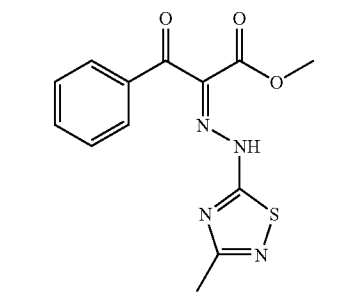
(DS-25)
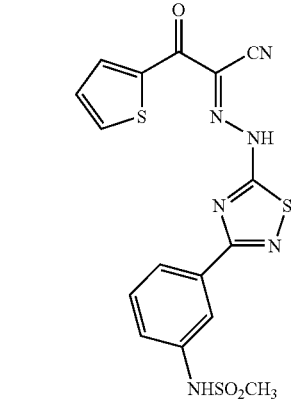
-continued
(DS-26)
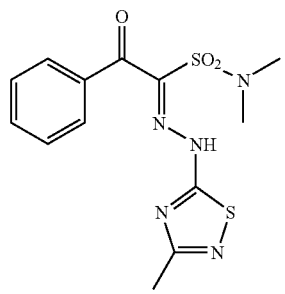
(DS-27)
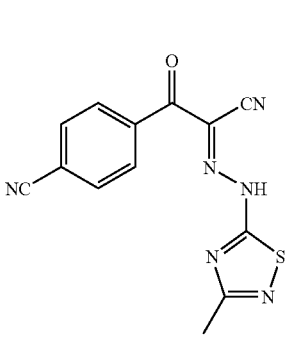
(DS-28)
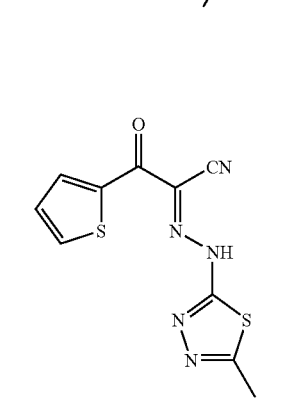
(DS-29)
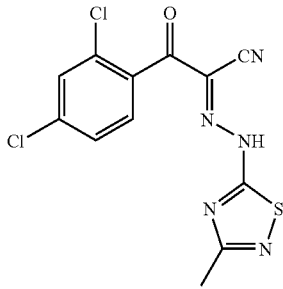
(DS-30)
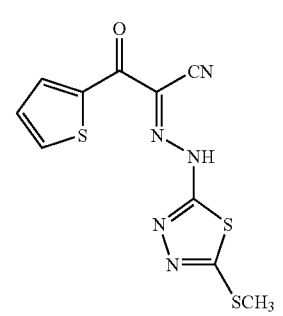

(DS-31)

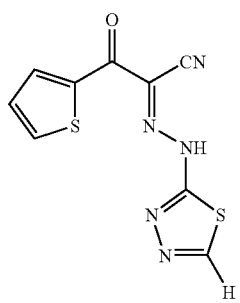

(DS-32)

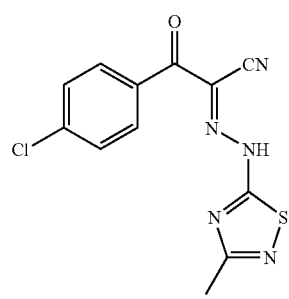

(DS-33)

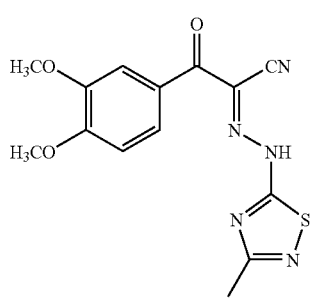

(DS-34)

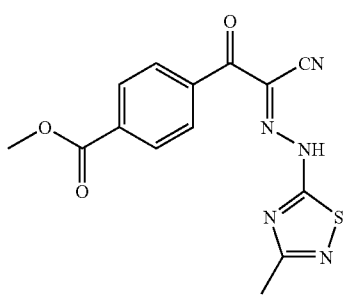

The compound represented by the formula (1) can be synthesized in a conventional manner, for example, by converting an aromatic amine compound (a) into the corresponding diazonium salt by using a nitrite and then reacting the resulting diazonium salt with an aromatic carbonyl compound (b) in accordance with the following reaction scheme.

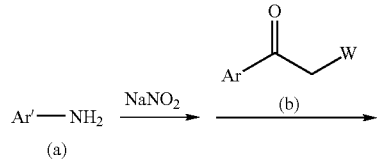

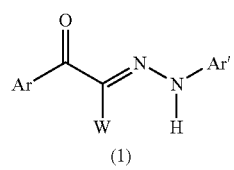

(1)

The $pK_a$ value of the direct dye (1) is preferably from 1.5 to 9, more preferably from 2 to 8, even more preferably from 2 to 7.5. The $pK_a$ value of the direct dye (1) can be used as a factor that determines the dyeing power of a dye.

The color provided by the direct dye (1) mainly ranges from a vivid yellow color to a gold color.

The content of the direct dye (1) is preferably from 0.0001 to 20 wt. %, more preferably from 0.001 to 20 wt. %, even more preferably from 0.05 to 10 wt. %, even more preferably from 0.1 to 5 wt. % in the whole composition (after mixing of all the component parts when the composition is a two-part type or three-part type. This will be applied equally hereinafter).

The direct dye (1) has excellent storage stability within a wide pH range of from 2 to 11 which is a pH range of ordinarily employed hair dyes, so that the hair dye composition of the present invention can be used at any pH in the above-described pH range. Use of the composition in a pH range of from 5 or greater is however preferred from the viewpoint of dyeing property. Moreover, owing to the high stability of the dissociative direct dye (1) against an alkali agent, the hair dye composition of the present invention can be used at a pH 8 or greater, preferably 8 to 11, at which the composition can exhibit a high dyeing property, so that even after long-term storage, it continues to have a high dyeing property without causing decomposition of the direct dye.

[Other dyes]

The hair dye composition of the present invention can additionally contain other direct dyes or oxidation dyes to change its color tone.

As other direct dyes, known direct dyes such as basic dyes, cationic dyes, nitro dyes and disperse dyes can be added. Specific examples include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in JP-A-58-2204 and JP-A-9-118832, and JP-A-8-501322 and JP-A-8-507545; and methine type cationic dyes having a cyanine structure represented by the following formulas:

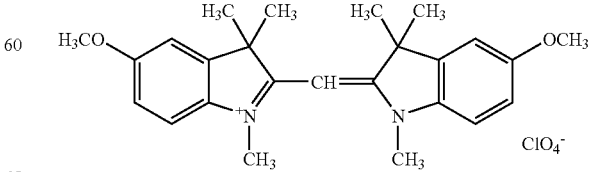

Yellow dye

-continued

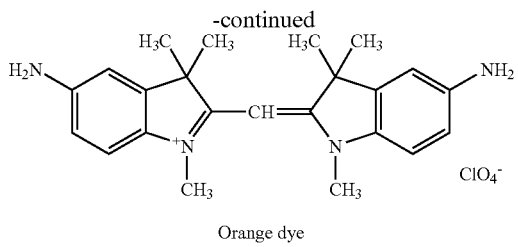

Orange dye

Direct dyes as described in, for example, JP-A-2002-275040, JP-A-2003-107222, JP-A-2003-107223, JP-A-2003-113055, JP-A-2004-107343, JP-A-2003-342139, and JP-A-2004-155746 can also be added.

When another direct dye is used in combination, the total content of the direct dye (1) and the other direct dye is preferably from 0.001 to 20 wt. %, more preferably from 0.01 to 20 wt. %, even more preferably from 0.05 to 10 wt. %, even more preferably from 0.1 to 5 wt. % in the whole composition.

In the hair dye composition of the present invention, an oxidation dye can be used in combination with the direct dye (1). Such combined use enables markedly vivid and strong hair dyeing which cannot be attained by the dyeing with an oxidation dye alone. As the oxidation dye, known color developers and couplers ordinarily employed for an oxidation hair dye can be employed.

Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, para-aminophenol, parametylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, meta-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

As each of the developer and coupler, two or more of the above-described developers or couplers are usable in combination. The total content of the developers or couplers in the whole composition is preferably from 0.0005 to 20 wt. %, more preferably from 0.001 to 19 wt. %, even more preferably from 0.01 to 15 wt. %, even more preferably from 0.5 to 10 wt. %.

The hair dye composition of the present invention may further contain an autoxidation dye typified by an indole or indoline.

The total content of the direct dye (1), another direct dye, oxidation dye and autoxidation dye in the hair dye composition of the present invention is preferably from 0.001 to 20 wt. %, more preferably from 0.01 to 20 wt. %, even more preferably from 0.5 to 15 wt. %.

[Other Components]

Examples of the alkali agent for use in the hair dye composition of the present invention include ammonia, alkanolamines such as monoethanolamine and isopropanolamine and salts thereof, guanidium salts such as guanidine carbonate; and hydroxides such as sodium hydroxide. The content of the alkali agent in the whole composition is preferably from 0.01 to 20 wt. %, more preferably from 0.1 to 10 wt. %, even more preferably from 0.5 to 5 wt. %.

The direct dye (1) for use in the present invention has excellent stability against an oxidizing agent so that it can be applied to the hair after mixed with the oxidizing agent. In other words, the hair dye composition of the present invention can be used as a two-part composition composed of a first part containing the direct dye (1) (which part may contain any other known direct dye and oxidation dye) and a second part containing an oxidizing agent. In this case, more vivid dyeing can be accomplished as a result of simultaneous dyeing and bleaching.

Examples of the oxidizing agent include hydrogen peroxide; persulfates such as ammonium persulfate, potassium persulfate and sodium persulfate; perborates such as sodium perborate; percarbonates such as sodium percarbonate; and bromates such as sodium bromate and potassium bromate. Of these, hydrogen peroxide is preferred from the viewpoints of hair bleaching property, and stability and effectiveness of the direct dye (1). Hydrogen peroxide may be used in combination with another oxidizing agent serving as an oxidizing aid. Combined use of hydrogen peroxide and a persulfate is preferred. The content of the oxidizing agent in the whole composition is preferably from 0.5 to 30 wt. %, more preferably from 1 to 20 wt. %. When hydrogen peroxide is used in combination with a persulfate, the content of hydrogen peroxide, the content of the persulfate, and the total content thereof are adjusted to fall within a range of preferably from 0.5 to 10 wt. %, from 0.5 to 25 wt. %, and from 1 to 30 wt. %, respectively.

The first part containing the direct dye (1) and the second part containing the oxidizing agent are mixed preferably at a volume ratio ranging from 2:1 to 1:3.

In order to change the color tone of the oxidation hair dye, it is also possible to add, prior to use or during use, a one-part hair dye composition containing the direct dye (1) to a known two-part oxidation hair dye or bleaching agent composed of a first part containing an alkali agent (which part may contain any other known direct dye) and a second part containing an oxidizing agent; or a known three-part oxidation hair dye or bleaching agent composed of a first part containing an alkali agent (which part may contain any other known direct dye), a second part containing an oxidizing agent, and a third part containing an oxidizing aid.

The hair dyeing property and shampoo fastness of the hair dye (1) can be enhanced by incorporating, in the hair dye composition, an organic solvent having a high hair penetration property selected from aromatic alcohols, lower alkylene carbonates, N-alkylpyrrolidones, and formamides. Examples of the aromatic alcohols include benzyl alcohol, phenethyl alcohol, γ-phenylpropyl alcohol, cinnamic alcohol, anis alcohol, p-methylbenzyl alcohol, α,α-dimethylphenethyl alcohol, α-phenylethanol, and phenoxyethanol. Examples of the lower alkylene carbonates include carbonates having a $C_{2-6}$ alkylene such as ethylene carbonate, propylene carbonate and butylene carbonate. Examples of the N-alkylpyrrolidones include N-methylpyrrolidone and N-ethylpyrrolidone. Examples of the formamides include N-cyclohexylformamide, N,N-dimethylformamide and N-methylformamide. From the viewpoints of the hair dyeing property and shampoo fastness, benzyl alcohol, benzyloxyethanol and propylene carbonate are preferred. Two or more of such organic solvents may be used in combination. Their content in the whole composition is preferably from 1 to 50 wt. %, more preferably from 5 to 45 wt. % from the viewpoints of hair dyeing property and shampoo fastness.

The hair dye composition of the present invention may contain a conditioning component suited for application to the hair. The amount thereof is from 0.01 to 30 wt. %, preferably from 0.1 to 20 wt. %, more preferably from 0.1 to 10 wt. % based on the whole composition. The conditioning component is typically a polymer or oil soluble or dispersible in a hair dye composition and it adheres to the hair during conditioning or when diluted with water or shampoo.

The conditioning component suited for use in the hair dye composition of the present invention is usually a conditioning component having characteristics as a silicone (such as silicone oil, cationic silicone, silicone gum or silicone resin) or an organic conditioning oil (such as a hydrocarbon oil, polyolefin or fatty acid ester), or combination thereof. A conditioning agent that forms dispersed liquid particles in an aqueous surfactant is also suited.

The conditioning component for use in the hair dye composition of the present invention is preferably an insoluble silicone conditioning agent. The particles of the silicone conditioning agent may contain volatile silicone or nonvolatile silicone or mixture thereof, but a nonvolatile silicone conditioning agent is preferred.

Preferred examples of the silicone oil used as the conditioning agent include polyalkylsiloxanes, polyarylsiloxanes, polyalkylarylsiloxanes, and polyether-siloxane copolymers, and mixtures thereof. Insoluble-nonvolatile silicone fluids having a hair conditioning effect are also usable.

Examples of the silicone oil include polyalkyl- or polyarylsiloxanes represented by the following formula (2):

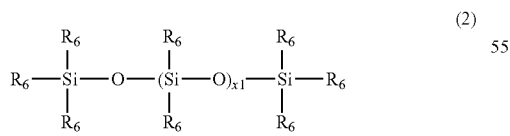

(wherein, $R_6$ represents an aliphatic group, preferably alkyl or alkenyl group, or an aryl group, which may be substituted or unsubstituted, and x1 stands for an integer from 1 to 8,000).

As the nonvolatile polyalkylsiloxane fluid, polydimethylsiloxanes having a low molecular weight can be used, for example. Such siloxanes are available, for example, as Viscasil R and SF96 series from General Electric and as Dow Corning 200 series from Dow Corning Corporation. The polyalkylarylsiloxane fluids usable as the conditioning component include, for example, polymethylphenylsiloxanes. Such siloxanes are available, for example, as SF1075 methylphenyl fluid from General Electric or as 556 Cosmetic Grade Fluid from Dow Corning Corporation. The polyethersiloxane copolymers usable as the conditioning component include, for example, a polypropylene-oxide modified polydimethylsiloxane (e.g., "Dow Corning DC-1248"). Ethylene oxide or a mixture of ethylene oxide and propylene oxide is usable when the concentrations of ethylene oxide and polypropylene oxide are sufficiently low to prevent their dissolution in water or various compositions described herein.

Examples of the alkylamino-substituted silicone preferably employed as the conditioning component include, but not limited to, alkylamino-substituted silicone represented by the below-described formula (3). This polymer is also known as amodimethicone.

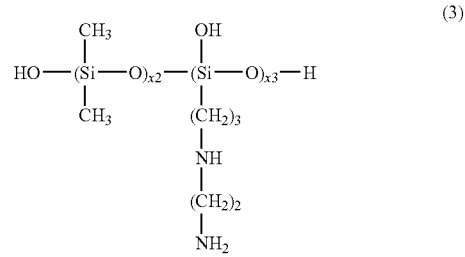

(wherein, x2 and x3 each stands for an integer)

Examples of the cationic silicone include polymers known as trimethylsilylamodimethicone represented by the following formula (4):

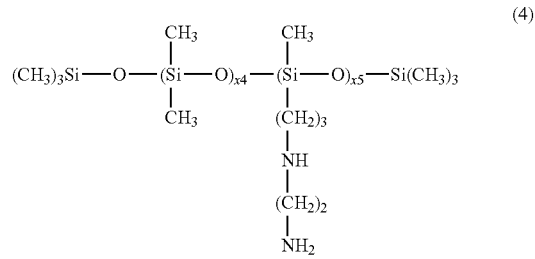

(wherein, x4 and x5 each stands for an integer).

Examples of the other silicone cationic polymers usable as the conditioning component include those represented by the following formula (5):

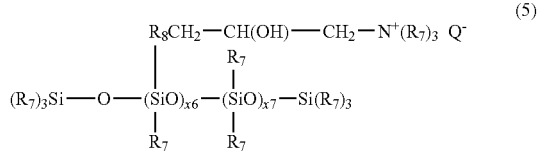

(wherein, $R_7$ represents a $C_{1-18}$ hydrocarbon group (preferably, an alkyl group such as methyl, or an alkenyl group), $R_8$ represents an alkylene or alkyleneoxy group (preferably a $C_{1-18}$ alkylene or $C_{1-18}$ alkyleneoxy group, more preferably a $C_{1-8}$ alkyleneoxy group), $Q^-$ represents a halide ion (preferably, a chloride ion), x6 is a statistic average and stands for from 2 to 20 (preferably from 2 to 8), and x7 is a statistical average and stands for from 20 to 200 (preferably from 20 to 50)).

Another silicone fluid suited as the conditioning component is an insoluble silicone gum. The silicone gum has typically an average molecular weight exceeding 200,000, preferably from 200,000 to 1,000,000. Specific examples of the silicone gum include, but are not limited to, polydimethylsiloxane, polydimethylsiloxane/methylvinylsiloxane copolymer, and polydimethylsiloxane/diphenylsiloxane/methylvinylsiloxane copolymer and mixtures thereof.

The conditioning component for use in the hair dye composition of the present invention can contain a silicone resin. The resin is composed of a highly crosslinked polymeric siloxane system. The crosslink is formed by adding a trifunctional or tetrafunctional silane to either one or both of monofunctional and bifunctional silanes during the preparation of a silicone resin.

The conditioning component for use in the hair dye composition of the present invention can further contain at least one organic conditioning oil. The content thereof in the composition is from 0.05 to 3 wt. %, preferably from 0.08 to 1.5 wt. %, more preferably from 0.1 to 1 wt. %. The organic conditioning oil may be used either singly or in combination with another conditioning component such as the above-described silicone. The conditioning oil can give luster and gloss to the hair and moreover, it can improve the nonsticky feel of the hair itself during combing.

The organic conditioning oil suited as the conditioning component is preferably a low-viscosity and water-insoluble liquid and is selected from hydrocarbon oils, polyolefins, and aliphatic esters and mixtures thereof. Such an organic conditioning oil has a viscosity as measured at 40° C. of preferably from 1 to 200 mPa·s, more preferably from 1 to 100 mPa·s, even more preferably from 2 to 50 mPa·s.

Examples of the organic conditioning oils suited as the conditioning component in the composition of the present invention include hydrocarbon oils having at least 10 carbon atoms such as cyclic hydrocarbons, linear aliphatic hydrocarbons (saturated or unsaturated), and branched aliphatic hydrocarbons (saturated or unsaturated). Examples also include polymers and mixtures of them. Linear hydrocarbon oils have preferably from 12 to 19 carbon atoms. Branched hydrocarbon oils include hydrocarbon polymers and they have typically more than 19 carbon atoms.

The organic conditioning oil for use in the composition of the present invention may contain a liquid polyolefin, more preferably, a liquid poly-α-olefin, even more preferably a hydrogenated liquid poly-α-olefin. The polyolefin usable as the organic conditioning oil is prepared by polymerizing a $C_{4-14}$, preferably $C_{6-12}$ olefin monomer.

Examples of other suitable organic conditioning oil used as the conditioning agent of the composition of the present invention include aliphatic esters having at least 10 carbon atoms. Examples of such aliphatic esters include esters having a hydrocarbon chain derived from a fatty acid and an alcohol (for example, monoesters, polyol esters, and di- and tri-carboxylate esters). The hydrocarbon group of these aliphatic esters may have another compatible functional portion such as an amide or alkoxy group (for example, ethoxy or another bond) or may be covalently-bonded thereto.

In the composition of the present invention, alkyl and alkenyl esters of a fatty acid having a $C_{10-22}$ aliphatic chain, aliphatic alcohol-carboxylate esters having an aliphatic chain derived from a $C_{10-22}$ alkyl and/or alkenyl alcohol, and mixtures thereof are suitably employed. Specific examples of preferred aliphatic esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

The hair dye composition of the present invention may contain at least one conditioning polymer which is suited for application to the hair, is organic cationic, and is adhesive. The amount thereof in the composition is from 0.02 to 5 wt. %, preferably from 0.05 to 3 wt. %, more preferably from 0.1 to 2 wt. %, even more preferably from 0.5 to 1 wt. %. The composition may further contain an anionic, nonionic and/or amphoteric polymer. In this case, the total amount of these polymers falls within the above-described range whether what polymer is chosen.

Any anionic counterions may be used in association with the cationic polymers insofar as the cationic polymers remain dissolved in the composition, and insofar as the counterions are physically and chemically compatible with the essential component of the hair dye composition or do not extremely impair the performance, stability or aesthetics of products. Examples of such counterions include, but are not limited to, halide ions (such as chloride ion, fluoride ion, bromide ion, and iodide ion), sulfate ions, and methylsulfate ions, and mixtures thereof. Examples of cationic polymers which may be suitably used for the hair dye composition of the present invention include, but are not limited to, cationic polysaccharides (such as cationic cellulose derivatives and cationic guars), copolymers of a vinyl monomer, vinylpyrrolidone copolymers, cationic proteins, and certain polymeric quaternary salts. Such cationic polymers will next be described in detail.

Cationic polymers preferably used for the hair dye composition of the present invention are polymers known as cationic polysaccharides. Cationic polysaccharides are polymers composed of a $C_5$ to $C_6$ sugar and a derivative cationized by grafting a cationic group onto a polysaccharide backbone. They include homopolymers, copolymers and terpolymers of a quaternary ammonium or cationic amine-substituted monomer unit. The above-described polymer may contain such a monomer unit and, if necessary, another non-cationic monomer unit. The polysaccharide may be composed of one or two or more sugars. The cationic amine may be selected from primary, secondary, or tertiary amine (preferably secondary or tertiary amine), depending upon the particular species and the selected pH of the hair dye composition. The monomers may be either in linear or branched arrangement. A cationic nitrogen-containing group may be added to any of these monomer units, but it is preferred that some of the monomer units do not have such groups.

The cationic polysaccharide polymers include the cationic celluloses and cationic starches which will be described below.

Preferred examples of the polysaccharide cationic polymers for use in the hair dye composition of the present invention include cationic cellulose derivatives and cationic starch derivatives. Such cationic polymers include polymers represented by the formula (6):

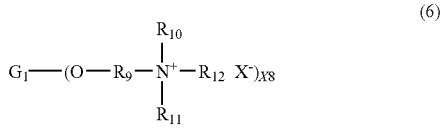

(wherein, $G_1$ is an anhydroglucose residue (such as a starch or cellulose anhydroglucose residue); $R_9$ represents an alkylene, oxyalkylene, polyoxyalkylene, or hydroxyalkylene group, or a combination thereof; $R_{10}$, $R_{11}$ and $R_{12}$ each independently represents an alkyl, aryl, alkylaryl, arylalkyl, alkoxyalkyl, or alkoxyaryl group, each group having up to 18 carbon atoms, and $R_{10}$, $R_{11}$ and $R_{12}$ have, as the total number of carbon atoms of cationic groups (i.e. the sum of the carbon atoms of $R_{10}$, $R_{11}$ and $R_{12}$), preferably 20 or less; x8 stands for an integer; and $X^-$ represents an anionic counterion).

Preferred cationic polymers include, but are not limited to, polymers available from Amerchol Corporation, that is, Polymer JR and LR series, and Polyquaternium 10 (for example, "JR30M", product of Amerchol Corporation) that is a salt of hydroxyethyl cellulose reacted with trimethylammonium-substituted epoxide and known in the industry (CTFA). Polyquaternium 10 polymers preferably usable here as the cationic polymer typically have a charge density from about 0.3 to 3 meq/g and a molecular weight from about 200,000 to 1,500,000. Further examples of preferred cationic celluloses include, but are not limited to, Polyquaternium 24 (for example, "Polymer LM 200", product of Amerchol Corporation), that is, a polymeric quaternary ammonium salt of hydroxyethyl cellulose reacted with lauryldimethylammonium-substituted epoxide and known in the industry (CTFA).

Other examples of the cationic polysaccharide polymers suited for use in the hair dye composition of the present invention include cationic guar polymers. Guars are cationically substituted galactomannan (guar) gum derivatives. Such derivatives have a molecular weight ranging typically from 50,000 to 2,500,000, preferably from 50,000 to 1,000,000, more preferably from 50,000 to 700,000.

Guar gum for use in preparing these guar gum derivatives can be obtained as a natural material available typically from the seeds of a guar tree. The guar molecule itself is a linear mannan and single membered galactose units are branched into alternate mannose units at certain intervals. The mannose units are each linked in a β(1-4) glycosidic linkage. The galactose branching takes place by means of α(1-6) linkage. Cationic derivatives of the guar gums are available by the reaction between the hydroxy group of polygalactomannan and a reactive quaternary ammonium compound. The sufficient degree of substitution of the cationic group in the guar structure provides a preferred cationic charge density as described above.

The cationic guar polymer is, for example, guar hydroxypropyltrimethylammonium chloride represented by the following formula (7):

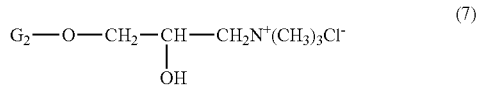

(wherein, $G_2$ represents guar gum)

Other suitable cationic polymers for use in the hair dye compositions of the present invention are copolymers of a vinyl monomer. This vinyl monomer has an amine or quaternary ammonium functional portion which has been protonated to be a cation and it reacts with a water soluble monomer. Examples of such a monomer include acrylamide, methacrylamide, alkyl and dialkyl acrylamides, alkyl and dialkyl methacrylamides, alkyl acrylates, alkyl methacrylates, vinyl caprolactone, and vinylpyrrolidone, and mixtures thereof. The alkyl and dialkyl substituted monomers have preferably a $C_{1-7}$ alkyl group, more preferably $C_{1-3}$ alkyl group. Other suitable monomers include vinyl esters, vinyl alcohols (prepared by the hydrolysis of polyvinyl acetate), maleic anhydride, propylene glycol, and ethylene glycol, and mixtures thereof.

Suitable examples of the amine and quaternary ammonium monomers which have been protonated to be a cation for inclusion in the cationic polymers of the hair dye composition of the present invention include vinyl compounds substituted by dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt or diallyl quaternary ammonium salt; and vinyl quaternary ammonium monomers having cyclic cationic nitrogen-containing rings (such as pyridinium, imidazolium, and quaternized pyrrolidone), for example, alkyl vinyl imidazolium, alkyl vinyl pyridinium and alkyl vinyl pyrrolidone salts. The alkyl portion of these monomers is preferably a lower alkyl such as $C_1$-$C_3$ alkyl.

Examples of the amine-substituted vinyl monomers suitable for use here include dialkylaminoalkyl acrylamides and dialkylaminoalkyl methacrylamides, wherein the alkyl group is preferably a $C_{1-7}$ hydrocarbon, more preferably a $C_{1-3}$ alkyl.

Other suitable cationic polymers for use in the hair dye composition of the present invention include copolymers of 1-vinyl-2-pyrrolidone and 1-vinyl-3-methylimidazolium salt (for example, chloride salt) known in the industry (CTFA) as Polyquaternium-16 (for example, "Luviquat FC 370", product of BASF Wyandotte Corporation); copolymers of 1-vinyl-2-pyrrolidone and dimethylaminoethyl methacrylate known in the industry (CTFA) as Polyquaternium 11 (for example, "Gafquat 755N", product of ISP Corporation); cationic diallyl quaternary ammonium-containing polymers known in the industry (CTFA) as Polyquaternium 6 (for example, dimethyldiallyl ammonium chloride homopolymer); copolymers of acrylamide and dimethyldiallylammonium chloride known in the industry (CTFA) as Polyquaternium 7; and mineral acid salts of aminoalkyl esters of a homopolymer or copolymer of an unsaturated $C_{3-5}$ carboxylic acid.

Examples of further cationic polymers for use in the hair dye composition of the present invention include cationic proteins such as lauryldimonium hydroxypropyl collagen (for example, "Croquat L", product of Croda Inc.) and cocodimonium hydroxypropyl hydrolyzed hair keratin (for example, "Croquat HH", product of Croda Inc). Examples of other cationic polymers include polymeric quaternary salts prepared by the reaction of adipic acid and dimethylaminopropylamine reacted with dichloroethyl ether known in the industry (CTFA) as Polyquaternium 2 (for example, "Mirapol AD-1", product of Rhodia), and polymeric quaternary salts prepared by the reaction of azelaic acid and dimethylaminopropylether known in the industry (CTFA) as Polyquaternium 18 (for example, "Mirapol AZ-1", product of Rhodia).

The hair dye composition of the present invention may further contain a polyalkylene glycol selected so as to be suited for the application to the hair and the amount thereof in the composition is from 0.005 to 1.5 wt. %, preferably from 0.025 to 1.2 wt. %, more preferably from 0.05 to 1 wt. %, even more preferably from 0.1 to 0.5 wt. %, Such a polyalkylene glycol is required to be physically and chemically compatible with the essential components as described herein, and not to impair the stability, aesthetics, or performances of products.

The polyalkylene glycol suited for use in the hair dye composition is represented by the formula (8):

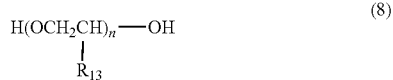

(8)

(wherein, $R_{13}$ represents a hydrogen atom or a methyl group, or combination thereof (preferably a hydrogen atom), and n is, on average, an integer from 1,500 to 120,000 (preferably from 1,500 to 50,000, more preferably from 2,500 to 25,000, even more preferably from 3,500 to 15,000)).

When $R_{13}$ represents a hydrogen atom, the material is a polymer of ethylene oxide and is also known as polyethylene glycol. When $R_{13}$ represents a methyl group, the material is a polymer of propylene oxide and is also known as polypropylene glycol. It has been understood that when $R_{13}$ represents a methyl group, various positional isomers of the resulting polymer can exist. Polyalkylene glycols suited for use here are polyethylene glycol, polypropylene glycol, and mixture thereof.

Specific examples of the polyethylene glycol polymer used for the stable and alkaline hair dye composition of the present invention include, but are not limited to, PEG 2M (of the above formula wherein $R_{13}$ represents hydrogen and n stands for 2,000 on average, for example, "Polyvox WSR N-10", product of Amerchol Corporation); PEG 5M (of the above formula wherein $R_{13}$ represents hydrogen and n stands for 5,000 on average, for example, "Polyvox WSR N-35" and "Polyvox WSR N-80", each product of Amerchol Corporation); PEG 7M (of the above formula wherein $R_{13}$ represents hydrogen and n stands for 7,000 on average, for example, "Polyvox WSR N-750", product of Amerchol Corporation); PEG 9M (of the above formula wherein $R_{13}$ represents hydrogen and n stands for 9,000 on average, for example, "Polyvox WSRN-3333", product of Amerchol Corporation); PEG 14M (of the above formula wherein $R_{13}$ represents hydrogen and n stands for 14,000 on average, for example, "Polyvox WSR N-3000", product of Amerchol Corporation); PEG 23M (of the above formula wherein $R_{13}$ represents hydrogen and n stands for 23,000 on average, for example, "Polyvox WSR N-12k", product of Amerchol Corporation); PEG 90M (of the above formula wherein $R_{13}$ represents hydrogen and n stands for 90,000 on average, for example, "Polyvox WSR 301", product of Amerchol Corporation); and PEG 100M (of the above formula wherein $R_{13}$ represents hydrogen and n stands for 100,000 on average, for example, "Carbowax PEG 4600", product of Amerchol Corporation). Preferred polyethylene glycols include PEG 7M, PEG 14M, PEG 25M, and PEG 90M, and mixtures thereof.

The hair dye composition of the invention may contain as a further optional component a chelating agent. It has been understood that a chelating agent component acts as a sequestering agent (by chelating or scavenging) of heavy metal ions. Such a component may also have calcium and magnesium chelation capacity, but preferably shows binding selectivity to heavy metal ions such as iron, manganese and copper. Such a chelating agent is useful for the hair dye composition as described herein because it provides hair coloring products with not only good storage stability but also controlled oxidizing action.

In the composition of the present invention, from 0.005 to 20 wt. %, preferably from 0.01 to 10 wt. %, more preferably from 0.05 to 2 wt. % of the chelating agent is typically present.

As the chelating agent used for such purposes, various chelating agents such as amino phosphonate ("Dequest", product of Monsanto Corporation), nitriloacetate, and hydroxyethyl-ethylene triamine are known.

Of these, diethylenetriamine penta(methylene phosphonate), ethylenediamine tri(methylene phosphonate), hexamethylenediamine tetra(methylene phosphonate) and hydroxyethylene-1,1-diphosphonate are preferred.

The heavy-metal-ion sequestering agent may be used in the form of alkali or alkaline earth metal salts of them.

The hair dye composition of the present invention may also contain a surfactant. An anionic, nonionic, cationic, amphoteric or zwitter-ionic surfactant can be incorporated in the hair dye composition of the present invention. The above-described surfactants are compatible if used in combination.

Examples of the anionic surfactant include sulfate, sulfonate, carboxylate and alkyl phosphate surfactants, which are typically used in the shampoos.

Examples of the sulfate anionic surfactants include well-known $C_{10-18}$ alkyl sulfates and appropriate ether sulfates such as $C_{12-14}$ alkyl ether sulfates and lauryl ether sulfates, preferably those having, in the molecule thereof, 1 to 4 ethylene oxide groups. Furthermore, monoglyceride (ether)sulfate, fatty acid amide sulfates which are prepared by ethoxylation and following sulfate introduction to the corresponding fatty acid alkanolamide; and their alkali salts as well as long-chain mono and dialkyl phosphates, which are mild detergents and can be applied to the hair can also be used.

Examples of suitable sulfonate anionic surfactants include α-olefin sulfonate and salts thereof. Additional examples include alkali salts of sulfosuccinic acid half-ester, for example, disodium salt of the monooctylsulfosuccinate and alkali salts of long-chain monoalkylethoxysulfosuccinate.

Examples of the suitable carboxylate surfactants include alkylpolyethercarboxylic acids and salts thereof, and alkamidopolyethercarboxylic acids and salts thereof. Such products are well known and have been on the market for a long time, for example, under the trade name "AKYPO" and "AKYPO-SOFT".

Also $C_{8-20}$ acyl isethionates and sulfofatty acids and esters thereof similar thereto can be used if they are mixed with other surfactants.

Also mixtures of several anionic surfactants are usable. Examples include mixtures (preferably 1:3 to 3:1 mixtures) of an α-olefin sulfate and a sulfosuccinate, and mixtures of an ether sulfate and a polyethercarboxylic acid or an alkylamidoethercarboxylic acid.

The concentration of the anionic surfactant is preferably from 0.5 to 10 wt. %, more preferably from 1 to 5 wt. %.

Other examples of suitable nonionic surfactants include alkylpolyglucosides; sorbitan esters such as polyethylene glycol sorbitan stearate; and fatty acid polyglycol esters and esters of a fatty acid and a polyglycol obtained by polymerizing a mixture of ethylene oxide and propylene oxide. They are on the market, for example, under the trade name of "Pluronics".

A further surfactant which can be used optionally is an amine oxide. Such an amine oxide belongs to the state of the art for a long time. Examples include $C_{12-18}$ alkyldimethylamine oxides such as lauryldimethylamine oxide; $C_{12-18}$ alkylamidopropylamide oxides and alkylamidoethylamine oxides; $C_{12-18}$ alkyldi(hydroxyethyl)amine oxides and alkyldi(hydroxypropyl)amine oxides; and amine oxides having, in the alkyl chain thereof, an ethylene oxide and/or propylene oxide group. Preferable amine oxides are those available, for example, under the trade name of "Ammonyx", "Aromox" or "Genaminox".

Further examples of the optional surfactant component include fatty acid mono- and di-alkanolamides such as coco fatty acid-monoethanolamide and myristic acid-monoisopropanolamide.

Examples of suitable amphoteric or zwitter-ionic surfactants include well-known betaines such as fatty acid-amidoalkylbetaines and sulfobetaines (such as lauryl hydroxysulfobetaine); and long-chain alkylamino acids such as cocoaminoacetate, cocoaminopropionate, sodium cocoamphopropionate and sodium cocoamphoacetate.

Examples of suitable cationic surfactants include long-chain quaternary ammonium compounds which may be used either singly or in combination, such as cetyltrimethylammonium chloride, dimethylstearylammonium chloride, trimethylacetylammonium bromide, stearyltrimethylammonium chloride, dimethylstearylbenzylammonium chloride, benzyltetradecyldimethylammonium chloride, dimethyl di-hydrogenated-tallow ammonium chloride, lauryldimethylbenzylammonium chloride, behenyltrimethylammonium chloride, lauryltrimethylammonium chloride, tris(oligooxyethyl)alkylammonium phosphate, and cetylpyridinium chloride.

The composition of the present invention can further contain a preservative such as oils and fats. Examples thereof include sunflower oil, almond oil, peach kernel oil, wheat germ oil, macadamia nut oil, evening primrose oil, jojoba oil, castor oil, olive oil, soybean oil, lanolin and derivatives thereof, and mineral oils such as paraffin oil and petrolatum, and a mixture thereof.

When the composition of the present invention is in the form of an emulsion, the composition may contain an ordinarily employed emulsifying agent. The composition of the present invention can contain a long-chain fatty acid. As the fatty acid, $C_{10-24}$, more preferably $C_{12-22}$ fatty acids are preferred, and they can be incorporated in an amount of from 0.5 to 15 wt. %, preferably from 1 to 10 wt. %, as calculated based on the whole composition. Of these, behenic acid and stearic acid are preferred, but other fatty acids such as myristic acid, palmitic acid, oleic acid or mixtures of natural or synthetic fatty acids such as coco fatty acid can also be added.

The hair dye composition of the present invention may contain a thickener at a level of from 0.05 to 20 wt. %, preferably from 0.1 to 10 wt. %, more preferably from 0.5 to 5 wt. % in the whole composition. The thickener suitable for use in the composition of the present invention is selected from oleic acid, cetyl alcohol, oleyl alcohol, sodium chloride, cetearyl alcohol and stearyl alcohol.

Water is a preferred diluent for the composition of the present invention. The composition according to the present invention may also contain one or more solvents as an additional material. Generally, solvents suited for use in the dye composition of the present invention are selected from those having compatibility with water. They are not harmful to the hair and/or scalp. Preferred examples of the solvent suited for use as an additional diluent include $C_{1-20}$ mono- or polyhydric alcohols and ethers thereof and glycerin, with monohydric and polyhydric alcohols and their ethers being preferred.

In these compounds, $C_{2-10}$ alcoholic residues are preferred. Examples of the preferred groups accordingly include ethanol, isopropanol, n-propanol, butanol, n-pentanol, propylene glycol, ethylene glycol monoethyl ether, 1,2-hexanediol, butoxyethanol, phenoxyethanol, benzyl alcohol, and propylene carbonate, and mixtures thereof. Examples of the more preferred solvent for the composition of the present invention include 1,2- and 1,3-propanediol-1-methoxy-2-propanol-1-ethoxy-2-propanol, 1,3- and 1,4-butanediol, diethylene glycol and monomethyl and monoethyl ether thereof, and dipropylene glycol and monomethyl and monoethyl ether thereof. The proportion of these diols is preferably from 0.5 and 30 wt. %, more preferably from 1 to 15 wt. %, even more preferably from 5 to 10 wt. % in the whole composition. In addition to these $C_{3-6}$ alkanediols and ethers thereof, monoalcohols such as ethanol, 1-propanol and 2-propanol; polyols such as glycerin and hexanetriol; ethylcarbitol; benzyl alcohol; benzyloxyethanol; propylene carbonate (4-methyl-1,3-dioxan-2-one); n-alkylpyrrolidones; and urea are also suited for use.

Water is a preferable main diluent in the composition of the present invention. The term "main diluent" as used herein means a diluent whose level in the composition is higher than the total level of the other diluents.

The amount of the solvents in the whole composition is preferably from 0.01 to 99 wt. %, preferably from 0.05 to 50 wt. %, more preferably from 0.1 to 15 wt. %, even more preferably from 0.2 to 5 wt. %.

The hair dye composition of the present invention can be prepared in a conventional manner into a one-part composition, a two-part composition composed of a first component part containing an alkali agent and a second component part containing an oxidizing agent, or a three-part composition composed of these two component parts and a powdery oxidizing agent such as persulfate. The direct dye (1) may be incorporated in either one or both of these component parts of the two-part or three-part composition. When the hair dye composition of the present invention is a one-part type, it is applied to the hair directly. When it is a two- or three-part type, it is applied to the hair after mixing these part components upon hair dyeing. Alternatively, the one-part composition containing the direct dye (1) may be mixed with the two-part or three-part composition during mixing of their components, followed by application to the hair.

The hair dye composition can be provided in the form of powder, transparent liquid, emulsion, cream, gel, paste, aerosol, aerosol foam, or the like. The viscosity of the composition when it is applied to the hair (after mixing of all the components when the composition is a two-part or three-part one) is preferably from 1,000 to 100,000 mPa·s, more preferably from 5,000 to 50,000 mPa·s, even more preferably from 10,000 to 40,000 mPa·s. The viscosity is measured at 20° C. by using a Brookfield rotary viscometer (No. 5 spindle, 5 rpm).

The hair dye composition of the present invention is usable for dyeing the human or animal hair. Such dyeing method includes applying the hair dye composition to the hair, rinsing the hair after completion of the dyeing, and drying the rinsed hair.

EXAMPLES

Synthesis Example 1

Compound (DS-6) was synthesized by the below-described process.

(1) Synthesis of crude (DS-6)

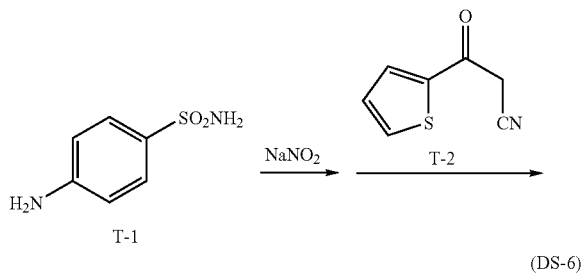

(DS-6)

To 17.2 g of Compound T-1 were added 80 mL of ice water and 25.7 mL of concentrated hydrochloric acid. An aqueous sodium nitrite solution (sodium nitrite/water=7.25 g/22 mL) was added dropwise to the resulting mixture while stirring under ice cooling at a temperature not exceeding 5° C. After completion of the dropwise addition, reaction was performed for 1 hour at 5° C. or less to prepare a diazonium solution of Compound T1. To 14.36 g of Compound T-2 were added 150 mL of methanol and 27.1 g of sodium acetate, followed by stirring while cooling in an ice-methanol bath. After dropwise addition of the above-described diazonium solution of Compound T-1 at a temperature not exceeding 15° C., the reaction was performed for 1 hour at 10° C. or less. To the reaction mixture was added 450 mL of water. Crystals thus precipitated were collected by filtration and rinsed with 500 mL of water to yield 31.8 g of crude crystals (DS-6) as pale yellow crystals.

(2) Purification of Compound (DS-6)

To 30.1 g of crude crystals (DS-6) were added 150 mL of methanol, followed by stirring to obtain a mixture in the form of a suspension. To the resulting suspension was added 25.1 mL of triethylamine. To the solution thus obtained was added aqueous hydrochloric acid (concentrated hydrochloric acid/water=17 mL/300 mL). Crystals thus precipitated were collected by filtration and washed with 100 ml of methanol/water with a mixture ratio of 2/1 to yield 25.6 g of (DS-6) as pale yellow crystals.

Synthesis Example 2

Compound (DS-7) was synthesized by the below-described process.

(1) Synthesis of crude (DS-7)

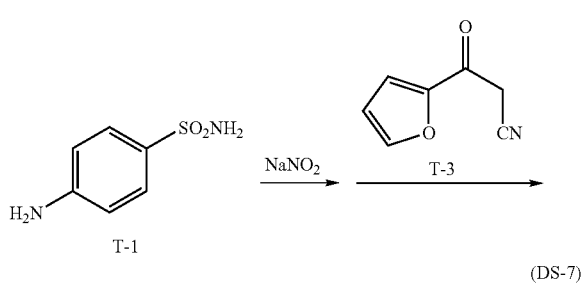

(DS-7)

To 17.2 g of Compound T-1 were added 80 mL of ice water and 25.74 mL of concentrated hydrochloric acid. An aqueous sodium nitrite solution (sodium nitrite/water=7.25 g/22 mL) was added dropwise to the resulting mixture while stirring at a temperature not exceeding 5° C. under ice cooling. After completion of the dropwise addition, reaction was performed for 1 hour at 5° C. or less to prepare a diazonium solution of Compound T1. To 12.83 g of Compound T-3 were added 130 mL of methanol and 27.1 g of sodium acetate, followed by stirring while cooling in an ice-methanol bath. After dropwise addition of the above-described diazonium solution of Compound T-1 at a temperature not exceeding 15° C., the reaction was performed for 1 hour at 10° C. or less. To the reaction mixture was added 450 mL of water. Crystals thus precipitated were collected by filtration and rinsed with 500 mL of water to yield 27.2 g of crude crystals of Compound (DS-7) as pale yellow crystals.

(2) Purification of Compound (DS-7)

To 27.5 g of crude (DS-7) crystals were added 130 mL of methanol, followed by stirring to obtain a mixture in the form of a suspension. To the resulting suspension was added 22.5 mL of triethylamine. To the solution thus obtained was added aqueous hydrochloric acid (concentrated hydrochloric acid/water=16 mL/260 mL). Crystals thus precipitated were collected by filtration and washed with 100 mL of methanol/water with a mixture ratio of 2/1 to yield 22.6 g of Compound (DS-7) as pale yellow crystals.

Synthesis Example 3

Compound (DS-8) was synthesized by the below-described process.

(1) Synthesis of crude (DS-8)

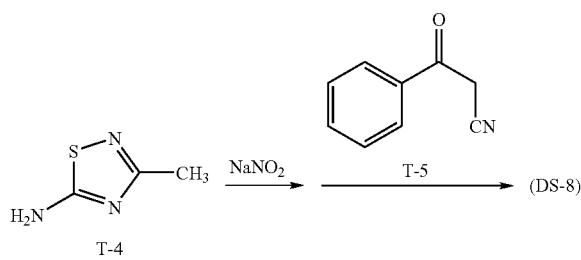

To 23.0 g of Compound T-4 was added 350 mL of phosphoric acid. After confirmation that the compound was dissolved at the bulk temperature of 45° C., the resulting solution was cooled in an ice bath. Then, 15.2 g of sodium nitrite was added in portions at a temperature not exceeding 10° C. After completion of the addition, the reaction was effected for 1 hour at 5° C. or less and an acetic acid solution of Compound T-5 (300 mL of acetic acid/26.2 g of T-5) was added dropwise to the reaction mixture at a temperature not exceeding 15° C. After the reaction was performed for 1 hour at 10° C. or less, 1450 mL of water was added to the reaction mixture. Crystals thus precipitated were collected by filtration and washed with 500 mL of water to yield 29.3 g of crude crystals of Compound (DS-8) as yellow crystals.

(2) Purification of Compound (DS-8)

To 27.1 g of crude crystals (DS-8) were added 300 mL of methanol, followed by stirring to obtain a mixture in the form of a suspension. To the resulting suspension was added 21 mL of triethylamine. To the solution thus obtained was added aqueous hydrochloric acid (concentrated hydrochloric acid/water=21 mL/160 mL). Crystals thus precipitated were collected by filtration and washed with 100 mL of methanol/water to yield 24.4 g of Compound (DS-8) as yellow crystals.

Examples 1 to 7

Foam-type hair dyes shown in Table 1 were prepared in a conventional manner.

TABLE 1

| (wt. %) | Examples | | | | | | |
|---|---|---|---|---|---|---|---|
| | 1 | 2 | 3 | 4 | 5 | 6 | 7 |
| Dissociative direct dye (DS-6) | 0.3 | 0.3 | 0.1 | 0.1 | 0.1 | 0.1 | 0.1 |
| Direct dye (E1) | — | 0.2 | — | 0.2 | 0.2 | 0.1 | — |
| Direct dye (E2) | — | 0.2 | — | 0.2 | 0.2 | 0.1 | 0.1 |
| HC Yellow 4 | — | — | 0.2 | — | 0.2 | — | — |
| Basic Yellow 87 | — | — | — | — | — | 0.1 | — |
| Basic Orange 31 | — | — | — | — | — | 0.2 | 0.1 |
| Basic Red 51 | — | — | — | — | — | — | 0.2 |
| Basic Red 76 | — | — | 0.3 | 0.3 | 0.3 | — | — |
| Ammonia (28 wt. %) | 8.0 | 8.0 | 8.0 | 8.0 | 8.0 | 8.0 | 8.0 |
| Isopropyl alcohol | 3.5 | 3.5 | 3.5 | 3.5 | 3.5 | 3.5 | 3.5 |
| Polyoxyethylene (23) lauryl ether | 0.5 | 0.5 | 0.5 | 0.5 | 0.5 | 0.5 | 0.5 |
| Benzyl alcohol | — | — | 8.0 | 8.0 | 8.0 | 8.0 | 8.0 |
| Oleic acid | 7.5 | 7.5 | 7.5 | 7.5 | 7.5 | 7.5 | 7.5 |
| LPG (4.0 kg/cm$^2$) | 10.0 | 10.0 | 10.0 | 10.0 | 10.0 | 10.0 | 10.0 |
| Purified water | Balance | Balance | Balance | Balance | Balance | Balance | Balance |
| Total | 100.0 | 100.0 | 100.0 | 100.0 | 100.0 | 100.0 | 100.0 |

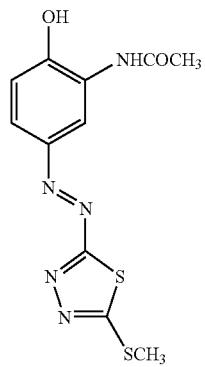

Direct dye (E1)

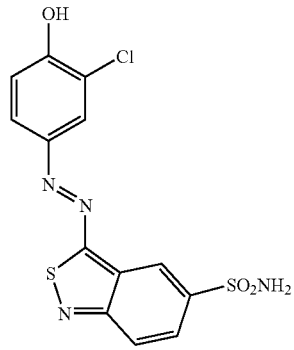

Direct dye (E2)

The above-described foam-type hair dyes were each applied to the goat hair at 30° C. After it was caused to act on the hair for 20 minutes, the resulting goat hair was shampooed with an ordinarily used shampoo, followed by drying. As a result of the observation of the color tone of the dyed hair, it was found that each composition had a good dyeing property and shampoo fastness.

Examples 8 to 14

One-part hair dyes shown in Table 2 were prepared in a conventional manner.

TABLE 2

| (wt %) | Examples | | | | | | |
|---|---|---|---|---|---|---|---|
| | 8 | 9 | 10 | 11 | 12 | 13 | 14 |
| Dissociative direct dye (DS-7) | 0.3 | 0.3 | 0.1 | 0.1 | 0.1 | 0.1 | 0.1 |
| Direct dye (E3) | — | 0.2 | — | 0.2 | — | 0.2 | 0.2 |
| Direct dye (E4) | — | 0.2 | — | 0.2 | — | 0.2 | 0.2 |
| HC Red 3 | — | — | 0.2 | 0.2 | 0.2 | — | 0.3 |
| Basic Yellow 57 | — | — | — | — | — | — | 0.1 |
| Basic Blue 99 | — | — | — | — | 0.1 | 0.1 | 0.1 |
| Ammonia (28 wt. %) | 8.0 | 8.0 | 8.0 | 8.0 | 8.0 | 8.0 | 8.0 |
| Isopropyl alcohol | 1.5 | 1.5 | 1.5 | 1.5 | 1.5 | 1.5 | 1.5 |
| Ethanol | 6.0 | 6.0 | 6.0 | 6.0 | 6.0 | 6.0 | 6.0 |
| Benzyl alcohol | 8.0 | 8.0 | 8.0 | 8.0 | 8.0 | 8.0 | 8.0 |
| PEG-12 | — | — | — | — | — | — | 0.5 |
| Ammonium chloride*[1] | q.s. | q.s. | q.s. | q.s. | q.s. | q.s. | q.s. |
| Hydroxypropyl xanthan gum*[2] | 2.0 | 2.0 | 2.0 | 2.0 | 2.0 | 2.0 | 2.0 |
| Polyether-modified silicone*[3] | — | 1.5 | 1.5 | — | 1.5 | 1.5 | 1.5 |
| Purified water | Balance | Balance | Balance | Balance | Balance | Balance | Balance |
| Total | 100.0 | 100.0 | 100.0 | 100.0 | 100.0 | 100.0 | 100.0 |

*[1]Amount to adjust pH to 10
*[2]"Rhaball Gum EX", product of Dainippon Pharmaceutical Co., Ltd.
*[3]"KF-6005", product of Shin-Etsu Chemical Co., Ltd.

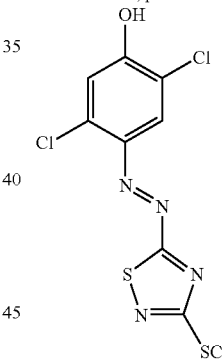

Direct dye (E3)

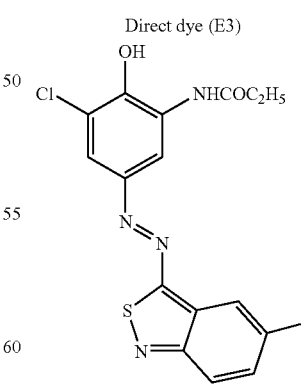

Direct dye (E4)

The above-described one-part hair dyes were each applied to the goat hair at 30° C. After it was caused to act on the hair for 20 minutes, the resulting goat hair was shampooed with an ordinarily used shampoo, followed by drying. As a result of the observation of the color tone of the dyed hair, it was found that each composition had a good dyeing property and shampoo fastness.

Examples 15 to 21

One-part hair dyes shown in Table 3 were prepared in a conventional manner.

TABLE 3

| (wt. %) | Examples |  |  |  |  |  |  |
|---|---|---|---|---|---|---|---|
|  | 15 | 16 | 17 | 18 | 19 | 20 | 21 |
| Dissociative direct dye (DS-1) | 0.1 | — | 0.1 | — | 0.1 | — | 0.1 |
| Dissociative direct dye (DS-8) | — | 0.01 | — | 0.1 | — | 0.01 | 0.1 |
| Direct dye (E3) | — | 0.2 | — | 0.2 | — | 0.2 | 0.2 |
| Direct dye (E4) | 0.2 | 0.2 | — | 0.1 | — | 0.2 | 0.1 |
| Red No. 106 | 0.3 | — | 0.2 | 0.2 | 0.2 | — | 0.1 |
| Yellow No. 403 (1) | — | 0.2 | — | — | — | — | — |
| Violet No. 401 | — | — | — | — | 0.1 | 0.1 | 0.1 |
| Benzyl alcohol | 2.5 | 2.5 | 2.5 | — | — | — | 1.0 |
| Benzyloxyethanol | — | — | — | 6.0 | 6.0 | 6.0 | 5.0 |
| Lactic acid | 3.0 | 3.0 | 3.0 | 3.0 | 3.0 | 3.0 | 3.0 |
| Hydroxypropyl xanthan gum*[4] | 2.0 | — | 2.0 | — | 2.0 | 2.0 | 2.0 |
| Hydroxyethyl cellulose*[5] | — | 1.6 | — | 2.0 | — | — | — |
| Carboxyvinyl polymer*[6] | — | 0.2 | — | — | — | — | — |
| Polyether-modified silicone*[7] | 1.5 | 1.5 | 1.5 | 1.5 | 1.5 | 1.5 | 1.5 |
| 48% Sodium hydroxide*[8] | q.s. | q.s. | q.s. | q.s. | q.s. | q.s. | q.s. |
| Purified water | Balance | Balance | Balance | Balance | Balance | Balance | Balance |
| Total | 100.0 | 100.0 | 100.0 | 100.0 | 100.0 | 100.0 | 100.0 |

*[4]Rhaball Gum EX, product of Dainippon Pharmaceutical Co., Ltd.
*[5]Natrosol 250MR, product of Hercules Incorporated.
*[6]Carbopol Ultrez 10 Polymer, product of Noveon, Inc.
*[7]KF-6005, product of Shin-Etsu Chemical Co., Ltd.
*[8]Amount to adjust pH to 3

The above-described one-part hair dyes were each applied to the goat hair at 30° C. After it was caused to act on the hair for 20 minutes, the resulting goat hair was shampooed with an ordinarily used shampoo, followed by drying. As a result of the observation of the color tone of the dyed hair, it was found that each composition had a good dyeing property and shampoo fastness.

Examples 22 to 26

Cream-type first part components of two-part hair dyes shown in Table 4 and second part components A of the hair dyes shown in Table 5 were prepared in a conventional manner.

TABLE 4

| (wt. %) | Examples |  |  |  |  |
|---|---|---|---|---|---|
|  | 22 | 23 | 24 | 25 | 26 |
| Dissociative direct dye (DS-13) | 0.5 | 0.3 | 0.2 | 0.2 | 0.1 |
| Direct dye (E1) | — | 0.2 | 0.1 | 0.1 | — |
| Direct dye (E5) | — | 0.1 | 0.1 | 0.1 | — |
| p-Phenylenediamine | 0.02 | 1.1 | — | 0.1 | 0.2 |
| N,N-bis(2-hydroxyethyl)para-phenylenediamine sulfate | — | 0.5 | — | — | 0.1 |
| p-Aminophenol | — | — | 0.35 | — | 0.1 |
| Resorcinol | 0.03 | 0.2 | — | 0.08 | 0.3 |
| 2-Methylresorcinol | — | — | 0.2 | — | — |
| m-Aminophenol | — | 0.4 | 0.2 | 0.02 | 0.2 |
| 1-Naphthol | 0.01 | — | — | — | 0.1 |
| Cetearyl alcohol | 9.0 | 9.0 | 9.0 | 9.0 | 9.0 |
| Sodium cetearyl sulfate | 1.0 | 1.0 | 1.0 | 1.0 | 1.0 |
| Cocamide MEA | 1.6 | 1.6 | 1.6 | 1.6 | 1.6 |
| Stearamide MEA | 1.6 | 1.6 | 1.6 | 1.6 | 1.6 |
| PEG-5 cocamide | 0.5 | 0.5 | 0.5 | 0.5 | 0.5 |
| Oleic acid | 1.0 | 1.0 | 1.0 | 1.0 | 1.0 |
| Hydroxyethyl cellulose*[9] | 0.5 | 0.5 | 0.5 | 0.5 | 0.5 |
| Sodium lauryl sulfate | 0.5 | 0.5 | 0.5 | 0.5 | 0.5 |
| Tetrasodium edetate | 0.2 | 0.2 | 0.2 | 0.2 | 0.2 |
| Ammonium chloride | 0.25 | 0.25 | 0.25 | 0.25 | 0.25 |
| Sodium sulfite | 0.25 | 0.25 | 0.25 | 0.25 | 0.25 |
| Panthenol | 0.3 | 0.3 | 0.3 | 0.3 | 0.3 |
| Hydrolyzed keratin | 0.15 | 0.15 | 0.15 | 0.15 | 0.15 |
| Sodium hydroxide*[10] | q.s. | q.s. | q.s. | q.s. | q.s. |
| Purified water | Balance | Balance | Balance | Balance | Balance |
| Total | 100.0 | 100.0 | 100.0 | 100.0 | 100.0 |

*[9]"Natrosol 250 MR", product of Hercules Incorporated
*[10]Amount to adjust the pH to 7.

TABLE 4-continued

| (wt. %) | Examples | | | | |
|---|---|---|---|---|---|
| | 22 | 23 | 24 | 25 | 26 |

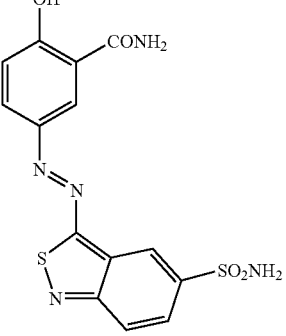

Direct dye (E5)

TABLE 5

| (wt. %) | Second part component A |
|---|---|
| Cetanol | 2.0 |
| Sodium lauryl sulfate | 1.0 |
| Hydrogen peroxide (50 wt. %) | 4.0 |
| Methylparaben | 0.1 |
| Phosphoric acid | Amount to adjust pH to 3.5 |
| Purified water | Balance |
| Total | 100.0 |

After 1 part by weight of the first part component was mixed with 2 parts by weight of the second part component A, the resulting mixture was applied to the goat hair at 30° C. and caused to act on the hair for 30 minutes. The resulting goat hair was shampooed with an ordinarily used shampoo, followed by drying. As a result of the observation of the color tone of the dyed hair, it was understood that each composition had a good dyeing property and shampoo fastness.

Examples 27 to 32

Combined Use with a Permanent Wave Solution

A first solution of a thioglycolic acid permanent wave solution shown in Table 6 was prepared in a conventional manner and it was used in combination with each of the cream-type first part components (Examples 22 to 26) shown in Table 4 and the second component part A shown in Table 5, or the second solution of the permanent wave solution shown in Table 7.

TABLE 6

| (wt. %) | First solution of thioglycolic acid permanent wave solution |
|---|---|
| Ammonium thioglycolate (50 wt. % aqueous solution) | 10.0 |
| Ammonia (28 wt. %) | 1.0 |
| Stearyl trimonium chloride | 0.1 |
| Propylene glycol | 5.0 |
| Disodium edetate | 0.1 |
| Purified water | Balance |
| Total | 100.0 |

TABLE 7

| (wt. %) | Second solution of permanent wave solution |
|---|---|
| Sodium bromate | 6.5 |
| POE hydrogenated oil | 0.5 |
| Citric acid | 0.03 |
| Trisodium citrate | 0.1 |
| Purified water | Balance |
| Total | 100.0 |

An adequate amount of the first solution of the thioglycolic acid type permanent wave solution was applied to the goat hair at 30° C. After it was caused to act on the hair for 30 minutes, an equal amount of each cream-type first part component of the two-part hair dyes obtained in Examples 20 to 24 was applied to the goat hair. The hair was wound around a curling rod and the shape of the hair was arranged. After the solution was caused to act on the hair for an additional 20 minutes, the second part component A or second permanent wave solution in an amount ranging from an equal to twice the amount was applied. After it was caused to act on the hair for 30 minutes, the resulting hair was shampooed with an ordinarily used shampoo, followed by drying. The hair thus dyed and permed was shaped as expected. At the same time, as a result of observation of the color tone, it was found that each composition had a good dyeing property and shampoo fastness.

Examples 33 to 42

The cream-type first part component of the two-part hair dyes shown in Table 8, and a second part component B and a second part component C shown in Table 9, were prepared in a conventional manner.

TABLE 8

| (wt. %) | Examples | | | | | | | | | |
|---|---|---|---|---|---|---|---|---|---|---|
| | 33 | 34 | 35 | 36 | 37 | 38 | 39 | 40 | 41 | 42 |
| Dissociative direct dye (DS-8) | 0.5 | 0.3 | 0.1 | 0.1 | 0.1 | 0.2 | 0.3 | 0.1 | 0.1 | 0.1 |
| Dissociative direct dye (DS-7) | — | — | — | 0.1 | — | 0.1 | — | — | — | 0.1 |
| Direct dye (E2) | — | 0.2 | — | 0.2 | 0.2 | — | 0.2 | — | 0.2 | 0.2 |
| Direct dye (E5) | — | 0.2 | — | 0.2 | 0.2 | — | 0.2 | — | 0.2 | 0.2 |
| Basic Yellow 87 | — | — | 0.1 | — | — | 0.1 | — | — | 0.1 | — |
| Basic Orange 31 | — | 0.1 | — | — | 0.1 | — | — | 0.1 | — | — |

TABLE 8-continued

| (wt. %) | Examples | | | | | | | | | |
|---|---|---|---|---|---|---|---|---|---|---|
| | 33 | 34 | 35 | 36 | 37 | 38 | 39 | 40 | 41 | 42 |
| Basic Red 51 | — | — | — | 0.1 | — | — | 0.1 | — | — | 0.1 |
| Yellow No. 403 (1) | — | — | — | 0.05 | 0.1 | — | 0.05 | 0.1 | — | 0.05 |
| Orange No. 205 | — | — | — | 0.05 | — | — | 0.05 | — | — | 0.05 |
| Violet No. 401 | — | — | — | — | — | — | — | — | 0.1 | — |
| Para-aminophenol | — | — | — | — | — | 0.3 | 0.1 | — | 0.1 | — |
| 2-Hydroxyethyl-p-phenylenediamine sulfate | — | — | — | — | — | 0.1 | — | — | — | 0.2 |
| Toluene-2,5-diamine sulfate | — | — | — | — | — | 0.2 | — | 0.2 | — | 0.3 |
| 5-Amino-orthocresol | — | — | — | — | — | 0.1 | — | 0.2 | 0.1 | — |
| Meta-aminophenol | — | — | — | — | — | 0.2 | 0.1 | — | — | 0.3 |
| 2,4-Diaminophenoxyethanol hydrochloride | — | — | — | — | — | — | — | — | — | 0.1 |
| Ammonia (28 wt. %) | 6.0 | 6.0 | 6.0 | 6.0 | 6.0 | 6.0 | 6.0 | 6.0 | 6.0 | 6.0 |
| Stearyl alcohol | 8.0 | 8.0 | 8.0 | 8.0 | 8.0 | 8.0 | 8.0 | 8.0 | 8.0 | 8.0 |
| Coconut oil fatty acid monoethanolamide | 4.5 | 4.5 | 4.5 | 4.5 | 4.5 | 4.5 | 4.5 | 4.5 | 4.5 | 4.5 |
| Glyceryl stearate (SE) | 1.3 | 1.3 | 1.3 | 1.3 | 1.3 | 1.3 | 1.3 | 1.3 | 1.3 | 1.3 |
| Ceteareth-30 | 4.0 | 4.0 | 4.0 | 4.0 | 4.0 | 4.0 | 4.0 | 4.0 | 4.0 | 4.0 |
| Sodium lauryl sulfate | 1.0 | 1.0 | 1.0 | 1.0 | 1.0 | 1.0 | 1.0 | 1.0 | 1.0 | 1.0 |
| Oleic acid | 2.0 | 2.0 | 2.0 | 2.0 | 2.0 | 2.0 | 2.0 | 2.0 | 2.0 | 2.0 |
| 1,2-Propanediol | 1.5 | 1.5 | 1.5 | 1.5 | 1.5 | 1.5 | 1.5 | 1.5 | 1.5 | 1.5 |
| Polyether-modified silicone*[11] | 1.5 | — | — | 1.5 | 1.5 | 1.5 | 1.5 | 1.5 | — | — |
| Hydrolyzed keratin | 0.5 | 0.5 | 0.5 | 0.5 | 0.5 | 0.5 | 0.5 | 0.5 | 0.5 | 0.5 |
| Panthenol | 0.8 | 0.8 | 0.8 | 0.8 | 0.8 | 0.8 | 0.8 | 0.8 | 0.8 | 0.8 |
| Tetrasodium edetate | 0.5 | 0.5 | 0.5 | 0.5 | 0.5 | 0.5 | 0.5 | 0.5 | 0.5 | 0.5 |
| Ammonium chloride*[12] | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |

*[11]"KF-6005", product of Shin-Etsu Chemical Co., Ltd.
*[12]Amount to adjust pH to 10.

TABLE 9

| (wt. %) | Common second part component B | Common second part component C |
|---|---|---|
| Cetanol | 2.0 | — |
| Sodium lauryl sulfate | 1.0 | — |
| Hydrogen peroxide (50 wt. %) | 12.0 | 12.0 |
| Methylparaben | 0.1 | — |
| Alkyl acrylate copolymer*[13] | — | 6.2 |
| Phosphoric acid | Amount to adjust pH to 3.5 | Amount to adjust pH to 3.5 |
| Purified water | Balance | Balance |
| Total | 100.0 | 100.0 |

*[13]"Aculyn 33", product of Rohm and Haas Company

After 1 part by weight of the first part component was mixed with 1 part by weight of the common second part component B or common second part component C, the resulting mixture was applied to the goat hair at 30° C. and was caused to act thereon for 30 minutes. The resulting hair was then shampooed with an ordinarily used shampoo, followed by drying. As a result of the observation of the color tone of the hair thus dyed, it was found that each composition had a good dyeing property and shampoo fastness.

Examples 43 to 52

The first part components of a cream type two-part hair dye were prepared as shown in Table 10 in a conventional manner.

TABLE 10

| (wt. %) | Examples | | | | | | | | | |
|---|---|---|---|---|---|---|---|---|---|---|
| | 43 | 44 | 45 | 46 | 47 | 48 | 49 | 50 | 51 | 52 |
| Dissociative direct dye (DS-12) | 0.3 | 0.3 | 0.1 | 0.1 | 0.1 | 0.3 | 0.3 | 0.1 | 0.1 | 0.1 |
| Direct dye (E5) | — | 0.2 | — | 0.2 | 0.2 | — | 0.2 | — | 0.2 | 0.2 |
| Direct dye (E6) | — | 0.2 | — | 0.2 | 0.2 | — | 0.2 | — | 0.2 | 0.2 |
| HC Red 3 | — | — | 0.2 | — | 0.2 | — | — | — | — | 0.2 |
| Basic Blue 99 | — | — | — | 0.1 | 0.1 | — | — | 0.2 | 0.1 | 0.1 |
| Para-aminophenol | — | — | — | — | — | 0.3 | 0.1 | — | 0.1 | — |
| Toluene-2,5-diamine sulfate | — | — | — | — | — | 0.2 | — | 0.2 | — | 0.1 |
| 5-Amino-orthocresol | — | — | — | — | — | 0.1 | — | 0.2 | 0.1 | 0.1 |
| Meta-aminophenol | — | — | — | — | — | 0.2 | 0.1 | — | — | 0.1 |
| Behenyl trimethylammonium chloride | 2.1 | 2.1 | 2.1 | 2.1 | 2.1 | 2.1 | 2.1 | 2.1 | 2.1 | 2.1 |

TABLE 10-continued

| (wt. %) | Examples | | | | | | | | | |
|---|---|---|---|---|---|---|---|---|---|---|
| | 43 | 44 | 45 | 46 | 47 | 48 | 49 | 50 | 51 | 52 |
| Liquid paraffin | 0.5 | 0.5 | 0.5 | 0.5 | 0.5 | 0.5 | 0.5 | 0.5 | 0.5 | 0.5 |
| Propylene glycol | 7.0 | 7.0 | 7.0 | 7.0 | 7.0 | 7.0 | 7.0 | 7.0 | 7.0 | 7.0 |
| Cetostearyl alcohol | 7.0 | 7.0 | 7.0 | 7.0 | 7.0 | 7.0 | 7.0 | 7.0 | 7.0 | 7.0 |
| Aqueous ammonia (28 wt. %) | 6.5 | 6.5 | 6.5 | 6.5 | 6.5 | 6.5 | 6.5 | 6.5 | 6.5 | 6.5 |
| Polyquaternium-10*[14] | 1.0 | — | 1.0 | — | 1.0 | 1.0 | — | 1.0 | — | 1.0 |
| Amino-modified silicon*[15] | 1.5 | 1.5 | — | — | 1.5 | 1.5 | 1.5 | — | — | 1.5 |
| Ammonium chloride*[16] | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |

*[14]"Ucare Polymer JR-400", product of Amerchol Corporation
*[15]"SM8704C", product of Dow Corning Toray Company
*[16]Amount to adjust pH to 10

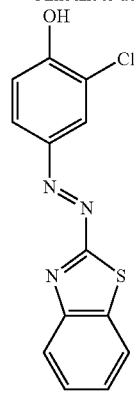

Direct dye (E6)

After 1 part by weight of the first part component was mixed with 1 part by weight of the common second part component B or common second part component C, the resulting mixture was applied to the goat hair at 30° C. and was caused to act thereon for 30 minutes. The hair thus dyed was then shampooed with an ordinarily used shampoo, followed by drying. As a result of the observation of the color tone of the hair, it was found that each composition had a good dyeing property and shampoo fastness.

Examples 53 to 62

The first part components of a liquid-type two-part hair dye were prepared as shown in Table 11 in a conventional manner.

TABLE 11

| (wt. %) | Examples | | | | | | | | | |
|---|---|---|---|---|---|---|---|---|---|---|
| | 53 | 54 | 55 | 56 | 57 | 58 | 59 | 60 | 61 | 62 |
| Dissociative direct dye (DS-13) | 0.5 | 0.4 | 0.3 | 0.2 | 0.2 | 0.3 | 0.3 | 0.3 | 0.1 | 0.1 |
| Direct dye (E1) | — | 0.3 | — | 0.2 | 0.3 | — | 0.2 | — | 0.2 | 0.2 |
| Direct dye (E2) | — | 0.3 | — | 0.1 | 0.2 | — | 0.2 | — | 0.2 | 0.2 |
| HC Yellow 4 | — | — | 0.4 | — | 0.1 | — | — | — | — | 0.2 |
| Basic Red 76 | — | — | — | 0.4 | 0.1 | — | — | 0.2 | 0.1 | 0.1 |
| Para-aminophenol | — | — | — | — | — | 0.3 | 0.1 | — | 0.1 | — |
| Toluene-2,5-diamine sulfate | — | — | — | — | — | 0.2 | — | 0.2 | — | 0.1 |
| 5-Amino-orthocresol | — | — | — | — | — | 0.1 | — | 0.2 | 0.1 | 0.1 |
| Meta-aminophenol | — | — | — | — | — | 0.2 | 0.1 | — | — | 0.1 |
| Ammonia (28 wt. %) | 8.0 | 8.0 | 8.0 | 8.0 | 8.0 | 8.0 | 8.0 | 8.0 | 8.0 | 8.0 |
| Ethanol | 10.0 | 10.0 | 10.0 | 10.0 | 10.0 | 10.0 | 10.0 | 10.0 | 10.0 | 10.0 |
| Propylene glycol | 10.0 | 10.0 | 10.0 | 10.0 | 10.0 | 10.0 | 10.0 | 10.0 | 10.0 | 10.0 |
| Oleic acid | 10.0 | 10.0 | 10.0 | 10.0 | 10.0 | 10.0 | 10.0 | 10.0 | 10.0 | 10.0 |
| Oleic diethanolamide | 8.0 | 8.0 | 8.0 | 8.0 | 8.0 | 8.0 | 8.0 | 8.0 | 8.0 | 8.0 |
| Oleyl alcohol | 2.0 | 2.0 | 2.0 | 2.0 | 2.0 | 2.0 | 2.0 | 2.0 | 2.0 | 2.0 |
| Polyoxyethylene (20) octyl dodecyl ether | 10.0 | 10.0 | 10.0 | 10.0 | 10.0 | 10.0 | 10.0 | 10.0 | 10.0 | 10.0 |
| Tetrasodium edetate | 0.1 | 0.1 | 0.1 | 0.1 | 0.1 | 0.1 | 0.1 | 0.1 | 0.1 | 0.1 |
| Ammonium chloride*[17] | q.s. | q.s. | q.s. | q.s. | q.s. | q.s. | q.s. | q.s. | q.s. | q.s. |

TABLE 11-continued

| (wt. %) | Examples | | | | | | | | | |
|---|---|---|---|---|---|---|---|---|---|---|
| | 53 | 54 | 55 | 56 | 57 | 58 | 59 | 60 | 61 | 62 |
| Polyether-modified silicone*[18] | 1.5 | — | — | 1.5 | 1.5 | 1.5 | 1.5 | 1.5 | — | — |
| Purified water | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 |

*[17]Amount to adjust pH to 10
*[18]"KF-6005", product of Shin-Etsu Chemical Co., Ltd.

After 1 part by weight of the first part component was mixed with 1 part by weight of the common second part component B or common second part component C, the resulting mixture was applied to the goat hair at 30° C. and was caused to act thereon for 30 minutes. The hair thus dyed was shampooed with an ordinarily used shampoo, followed by drying. As a result of the observation of the color tone of the hair, it was found that each composition had a good dyeing property and shampoo fastness.

Examples 63 to 71

The cream-type first part components for two-part hair dyes shown in Table 12 and color boosters shown in Table 13 were prepared in a conventional manner.

TABLE 12

| | (wt. %) | Examples | | | | | | | | |
|---|---|---|---|---|---|---|---|---|---|---|
| | | 63 | 64 | 65 | 66 | 67 | 68 | 69 | 70 | 71 |
| First part | Dissociative direct dye (DS-13) | 0.5 | 0.4 | 0.3 | 0.2 | 0.2 | 0.3 | 0.1 | 0.1 | 0.1 |
| | Direct dye (E5) | — | 0.2 | — | 0.2 | 0.2 | — | 0.2 | 0.2 | 0.2 |
| | Direct dye (E6) | — | 0.2 | — | 0.2 | 0.2 | — | 0.2 | 0.2 | 0.2 |
| | HC Red 3 | — | — | 0.2 | — | 0.2 | — | — | 0.2 | 0.2 |
| | Basic Blue 99 | — | — | — | 0.1 | 0.1 | — | 0.1 | 0.1 | 0.1 |
| | Para-aminophenol | — | — | — | — | — | 0.3 | 0.1 | — | — |
| | Toluene-2,5-diamine sulfate | — | — | — | — | — | 0.2 | — | 0.1 | 0.1 |
| | 5-Amino-orthocresol | — | — | — | — | — | 0.1 | 0.1 | 0.1 | 0.1 |
| | Meta-aminophenol | — | — | — | — | — | 0.2 | — | 0.1 | 0.1 |
| | Behenyl trimethylammonium chloride | 2.1 | 2.1 | 2.1 | 2.1 | 2.1 | 2.1 | 2.1 | 2.1 | 2.1 |
| | Liquid paraffin | 0.5 | 0.5 | 0.5 | 0.5 | 0.5 | 0.5 | 0.5 | 0.5 | 0.5 |
| | Propylene glycol | 7.0 | 7.0 | 7.0 | 7.0 | 7.0 | 7.0 | 7.0 | 7.0 | 7.0 |
| | Cetostearyl alcohol | 7.0 | 7.0 | 7.0 | 7.0 | 7.0 | 7.0 | 7.0 | 7.0 | 7.0 |
| | Aqueous ammonia (28 wt. %) | 6.5 | 6.5 | 6.5 | 6.5 | 6.5 | 6.5 | 6.5 | 6.5 | 6.5 |
| | Polyquaternium-10*[19] | 1.0 | — | 1.0 | — | 1.0 | 1.0 | — | 1.0 | 1.0 |
| | Amino-modified silicone*[20] | 1.5 | 1.5 | — | — | 1.5 | 1.5 | 1.5 | — | — |
| | Purified water | Balance | Balance | Balance | Balance | Balance | Balance | Balance | Balance | Balance |
| | Total | 100.0 | 100.0 | 100.0 | 100.0 | 100.0 | 100.0 | 100.0 | 100.0 | 100.0 |

*[19]"Ucare Polymer JR-400", product of Amerchol Corporation
*[20]"SM8704C", product of Dow Corning Toray Company

TABLE 13

| | (wt. %) | Examples | | | | | | | | |
|---|---|---|---|---|---|---|---|---|---|---|
| | | 63 | 64 | 65 | 66 | 67 | 68 | 69 | 70 | 71 |
| Color Booster | Dissociative direct dye (DS-8) | 0.6 | 0.6 | 0.6 | — | — | 0.4 | 0.4 | 0.4 | 0.5 |
| | Direct dye (E1) | 0.2 | 0.4 | — | 0.6 | — | — | — | — | — |
| | Direct dye (E4) | 0.4 | — | — | — | 0.6 | — | — | — | — |
| | Aqueous ammonia (28 wt. %) | 2.0 | 2.0 | 2.0 | 2.0 | 2.0 | 2.0 | 2.0 | 2.0 | — |
| | PEG-8 | 3.0 | 3.0 | 3.0 | 3.0 | 3.0 | 3.0 | 3.0 | 3.0 | — |
| | Sodium sulfate | — | — | — | — | — | — | — | — | 48.5 |
| | Sodium bisulfate | — | — | — | — | — | — | — | — | 50.0 |
| | Carboxymethylcellulose sodium *21 | — | — | — | — | — | — | — | — | 1.0 |
| | Purified water | Balance | Balance | Balance | Balance | Balance | Balance | Balance | Balance | — |
| | Total | 100.0 | 100.0 | 100.0 | 100.0 | 100.0 | 100.0 | 100.0 | 100.0 | 100.0 |

*21: "CMC Daicel 1150", product of Daicel Chemical Industries, Ltd.

After 1 part by weight of the first part component was mixed with 1 part by weight of the common second part component B or common second part component C, the resulting mixture was applied to the goat hair at 30° C. and was caused to act thereon for 30 minutes. The hair thus dyed was then shampooed with an ordinarily used shampoo, followed by drying. As a result of the observation of the color tone of the hair, it was found that each composition had a good dyeing property and shampoo fastness.

After 1 part by weight of the first part component was mixed with 1 part by weight of the common second part component B or common second part component C and 0.1 part by weight of a color booster corresponding to the first part component, the resulting mixture was applied to the goat hair at 30° C. and was caused to act thereon for 30 minutes. The hair thus dyed was then shampooed with an ordinarily used shampoo, followed by drying. As a result of the observation of the color tone of the hair, it was found that each composition had a good dyeing property and shampoo fastness.

Examples 72 to 77

Cream-type first part components and third part components for three-part hair dyes shown in Table 14 were prepared in a conventional manner.

TABLE 14

|  |  (wt. %) | Examples | | | | | |
| --- | --- | --- | --- | --- | --- | --- | --- |
|  |  | 72 | 73 | 74 | 75 | 76 | 77 |
| First part | Dissociative direct dye (DS-8) | 0.3 | 0.3 | 0.3 | — | — | 0.0001 |
|  | Direct dye (E6) | — | 0.2 | 0.1 | 0.3 | — | — |
|  | Direct dye (E3) | — | — | 0.2 | — | 0.3 | 0.3 |
|  | Ammonia (28 wt. %) | 8.0 | 8.0 | 8.0 | 8.0 | 8.0 | 8.0 |
|  | Stearyl alcohol | 8.0 | 8.0 | 8.0 | 8.0 | 8.0 | 8.0 |
|  | Coconut oil fatty acid monoethanolamide | 4.5 | 4.5 | 4.5 | 4.5 | 4.5 | 4.5 |
|  | Glyceryl stearate (SE) | 1.3 | 1.3 | 1.3 | 1.3 | 1.3 | 1.3 |
|  | Ceteareth-30 | 4.0 | 4.0 | 4.0 | 4.0 | 4.0 | 4.0 |
|  | Sodium lauryl sulfate | 1.0 | 1.0 | 1.0 | 1.0 | 1.0 | 1.0 |
|  | Oleic acid | 2.0 | 2.0 | 2.0 | 2.0 | 2.0 | 2.0 |
|  | 1,2-Propanediol | 1.5 | 1.5 | 1.5 | 1.5 | 1.5 | 1.5 |
|  | Polyether-modified silicone*[22] | 1.5 | — | — | 1.5 | 1.5 | 1.5 |
|  | Hydrolyzed keratin | 0.5 | 0.5 | 0.5 | 0.5 | 0.5 | 0.5 |
|  | Panthenol | 0.8 | 0.8 | 0.8 | 0.8 | 0.8 | 0.8 |
|  | Tetrasodium edetate | 0.5 | 0.5 | 0.5 | 0.5 | 0.5 | 0.5 |
|  | Ammonium chloride*[23] | q.s. | q.s. | q.s. | q.s. | q.s. | q.s. |
|  | Purified water | Balance | Balance | Balance | Balance | Balance | Balance |
|  | Total | 100.0 | 100.0 | 100.0 | 100.0 | 100.0 | 100.0 |
| Third part | Dissociative direct dye (DS-8) | — | — | — | 0.3 | 0.3 | — |
|  | Direct dye (E2) | — | 0.2 | — | — | — | — |
|  | Direct dye (E3) | — | — | — | — | 0.3 | — |
|  | Ammonium persulfate*[24] (g) | 5.0 | 5.0 | 5.0 | 5.0 | 5.0 | 5.0 |

*[22]"KF-6005", product of Shin-Etsu Chemical Co., Ltd.
*[23]Amount to adjust pH to 10
*[24]Purity: 95% (powder)

After 1 part by weight of the first part component was mixed with 1 part by weight of the common second part component B or common second part component C and 0.3 to 1 part by weight of the third part component, the resulting mixture was applied to the goat hair at 30° C. and was caused to act thereon for 30 minutes. The hair thus dyed was then shampooed with an ordinarily used shampoo, followed by drying. As a result of the observation of the color tone of the hair, it was found that each composition had a good dyeing property and shampoo fastness.

The invention claimed is:

1. A hair dye composition comprising a dissociative direct dye of the following formula (1):

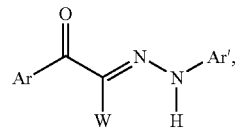

(1)

wherein Ar and Ar' are each free of a carboxy group, a sulfo group and a quaternary ammonium group; Ar represents an aromatic or a heterocyclic aromatic group which may have a substituent, while Ar' represents an aromatic group which may have, as a substituent, an alkyl group or an electron withdrawing group, or a heterocyclic aromatic group represented by any one of the following formulas (Cp-1) to (Cp-4):

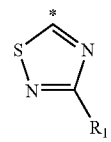

(Cp-1)

-continued

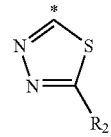

(Cp-2)

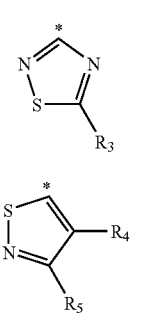

(Cp-3)

(Cp-4)

* means a bonding position to a nitrogen atom in the formula (1), $R_1$ to $R_5$ each represents a hydrogen atom, a $C_1$-$C_8$ alkyl group, an alkoxy group, an alkoxyalkyl group, a hydroxyalkyl group, an aryl group, an aryloxy group, an alkylthio group or an arylthio group, and $R_4$ and $R_5$ may be the same or different and may be coupled to form a saturated ring, an aromatic ring or a heteroaromatic ring which may have a substituent together with two vicinal carbon atoms; and W represents an electron withdrawing group; or a salt thereof, wherein when Ar is a furyl group, Ar' is not represented by the formula (Cp-1).

2. The hair dye composition according to claim 1, which comprises the dissociative direct dye represented by the formula (1), wherein Ar represents a phenyl group which may be substituted by a halogen atom, an alkyl group, an alkoxy group, a cyano group, an acylamino group or a carbamoyl group; W represents a group selected from a nitro group, a cyano group, an acylamino group, an aminocarbonylamino group, a sulfamoylamino group, an alkylsulfonylamino group, an arylsulfonylamino group, a sulfamoyl group and a carbamoyl group; Ar' represents a phenyl group which may be substituted by a halogen atom, an alkyl group, an alkoxy group, a cyano group, an acylamino group, an aminocarbonylamino group, an alkoxycarbonylamino group, an aryloxycarbonylamino group, a sulfamoylamino group, an alkylsulfonylamino group, an arylsulfonylamino group, an alkoxycarbonyl group, a sulfamoyl group or a carbamoyl group, or a heterocyclic aromatic group represented by the formula (Cp-1), (Cp-2), or (Cp-4).

3. The hair dye composition according to claim 1 or 2, further comprising an alkali agent.

4. The hair dye composition according to claim 1 or 2, further comprising an oxidizing agent.

5. A hair dyeing method comprising applying a hair dye composition as described in claim 1 to the hair.

6. A hair dyeing method comprising applying a hair dye composition as described in claim 1 to the bleached hair.

7. The hair dye composition according to claim 1, wherein the group (Cp-4) is selected from the group consisting of 2,1-benzisothiazol-3-yl, isothiazolo[4,3-b]pyridin-3-yl, isothiazolo[4,3-c]pyridin-3-yl, isothiazolo[3,4-c]pyridin-3-yl, isothiazolo[3,4-b]pyridin-3-yl, isothiazolo[4,3-c]pyridazin-3-yl, isothiazolo[4,3-d]pyrimidin-3-yl, isothiazolo[3,4-b]pyrazin-3-yl, isothiazolo[3,4-d]pyridazin-3-yl, isothiazolo[3,4-d]pyrimidin-3-yl, and isothiazolo[3,4-c]pyridazin-3-yl.

8. The hair dye composition according to claim 1, wherein the group W in an electron withdrawing group having a Hammett $\sigma_p$ value of 0.1 or greater.

* * * * *